US012649745B2

United States Patent

Beurier et al.

(12) United States Patent
(10) Patent No.: US 12,649,745 B2
(45) Date of Patent: Jun. 9, 2026

(54) AMINO-PYRIMIDINE CYCLO-AMIDES

(71) Applicant: Hoffmann-La Roche Inc., Little Falls, NJ (US)

(72) Inventors: Angélica Beurier, Courtavon (FR); Luke Green, Basel (CH); Christian Kramer, Lörrach (DE); Dmitry Mazunin, Grenzach-Wyhlen (DE); Emmanuel Pinard, Linsdorf (FR); Hasane Ratni, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 496 days.

(21) Appl. No.: 18/062,892

(22) Filed: Dec. 7, 2022

(65) Prior Publication Data

US 2023/0123268 A1 Apr. 20, 2023

Related U.S. Application Data

(63) Continuation of application No. PCT/EP2021/065106, filed on Jun. 7, 2021.

(30) Foreign Application Priority Data

Jun. 8, 2020 (EP) .................................... 20178638

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC ............................ C07D 487/04; C07D 471/04
See application file for complete search history.

(56) References Cited

U.S. PATENT DOCUMENTS

| | | | |
|---|---|---|---|
| 2021/0363152 | A1 | 11/2021 | Baccei et al. |
| 2023/0112172 | A1 | 4/2023 | Brom et al. |
| 2023/0174516 | A1 | 6/2023 | Beurier et al. |

FOREIGN PATENT DOCUMENTS

| | | | |
|---|---|---|---|
| JP | 2019-518799 | A | 4/2019 |
| WO | 2021/043260 | A1 | 11/2021 |
| WO | 2018/212534 | A1 | 11/2022 |

OTHER PUBLICATIONS

Cancer [online], [retrieved on Jul. 6, 2007] Retrieved from the Internet, URL: http://www.nlm.nih.gov/medlineplus /cancer.html, pp. 1-10 (Jul. 6, 2007).
Golub et al., "Molecular Classification of Cancer: Class Discovery and Class Prediction by Gene Expression Monitoring," Science 286:531-537 (Oct. 15, 1999).
"International Preliminary Report on Patentability—PCT/EP2021/065111" (Report Issuance Date: Dec. 13, 2022; Chapter I), pp. 1-7 (Dec. 22, 2022).
"International Preliminary Report on Patentability—PCT/EP2021/065084" (Report Issuance Date: Dec. 13, 2022; Chapter I), pp. 1-7 (Dec. 22, 2022).
"International Search Report—PCT/EP2021/065084" (w/Written Opinion), pp. 1-11 (Jul. 29, 2021).
"International Search Report—PCT/EP2021/065111" (w/Written Opinion), pp. 1-11 (Sep. 17, 2021).
Lala et al., "Role of Nitric Oxide in Tumor Progression: Lessons from Experimental Tumors," Cancer and Metastasis Reviews, 17:91-106 (1998).
"International Preliminary Report on Patentability—PCT/EP2021/065106" (Report Issuance Date: Dec. 13, 2022; Chapter I), :pp. 1-7 (Dec. 22, 2022).
"International Search Report—PCT/EP2021/065106" (w/Written Opinion), :pp. 1-11 (Sep. 17, 2021).

*Primary Examiner* — Renee Claytor
*Assistant Examiner* — Christopher Lindsay Johnson
(74) *Attorney, Agent, or Firm* — Sarah E. Tully

(57) ABSTRACT

The invention provides novel compounds having the general formula (I)

(I)

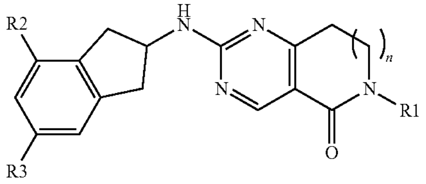

wherein $R^1$, $R^2$, $R^3$ and n are as defined herein, compositions including methods of making the compounds and using the compounds as ATX inhibitors.

9 Claims, No Drawings

AMINO-PYRIMIDINE CYCLO-AMIDES

CROSS-REFERENCE TO RELATED APPLICATIONS

This application is a continuation of International Patent Application No. PCT/EP2021/065106 filed on Jun. 7, 2021, which is entitled to the benefit of European Application No. EP20178638.1 filed on Jun. 8, 2020, the disclosures of which are incorporated herein by reference.

FIELD OF THE INVENTION

This invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

BACKGROUND OF THE INVENTION

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors.

The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

SUMMARY OF THE INVENTION

The present invention provides novel compounds of formula (I)

(I)

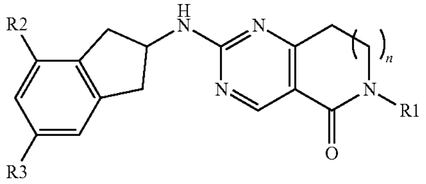

wherein $R^1$ is selected from the groups consisting of i) H,
ii) $C_{1-6}$-alkyl,
iii) $C_{3-8}$-cycloalkyl
iv) $C_{3-8}$-cycloalkylalkyl
v) $C_{1-6}$-alkoxy
vi) $C_{1-6}$-alkoxy-$C_{1-6}$-alkyl
vii) Heterocycloalkyl
viii) Heterocycloalkylalkyl
ix) Substituted $C_{3-8}$-cycloalkyl
x) Substituted $C_{3-8}$-cycloalkylalkyl
xi) Substituted Heterocycloalkyl
xii) Substituted Heterocycloalkylalkyl
xiii) halo-$C_{1-6}$-alkyl
xiv) hydroxy-$C_{1-6}$-alkyl wherein Substituted $C_{3-8}$-cycloalkyl or Subsisted Heterocycloalkyl are substituted with one or more substituents selected from H, $C_{1-6}$-alkyl, halogen, hydroxy, and $C_{1-6}$-carbonyl $R^2$ is selected from the group consisting of i) H,
ii) halogen,
iii) halo-$C_{1-6}$-alkyl
iv) $C_{1-6}$-alkyl;
v) cyano wherein at least one of $R^1$ and $R^2$ are other than H;

$R^3$ is selected from the groups consisting of i) H,
ii) halogen, and n is 0 or 1, or pharmaceutically acceptable salts.

Furthermore, the invention includes all racemic mixtures, all their corresponding enantiomers and/or optical isomers.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and- chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particularly, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

DETAILED DESCRIPTION OF THE INVENTION

The term "$C_{1-6}$-alkoxy" denotes a group of the formula —O—R', wherein R' is a $C_{1-6}$-alkyl group. Examples of $C_{1-6}$-alkoxy group include methoxy, ethoxy, n-propoxy, isopropoxy, n-butoxy, isobutoxy and tert-butoxy.

The term "$C_{1-6}$-alkoxy-$C_{1-6}$-alkyl" denotes a $C_{1-6}$-alkyl group wherein at least one of the hydrogen atoms of the $C_{1-6}$-alkyl group is replaced by a $C_{1-6}$-alkoxy group. Particular examples are methoxymethyl, methoxyethyl, ethoxymethyl, ethoxyethyl, iso-propoxymethyl and iso-propoxyethyl.

The term "$C_{1-6}$-alkyl" denotes a monovalent linear or branched saturated hydrocarbon group of 1 to 6 carbon atoms. In some embodiments, if not otherwise described, alkyl comprises 1 to 6 carbon atoms ($C_{1-6}$ alkyl), or 1 to 4 carbon atoms ($C_{1-4}$-alkyl). Examples of $C_{1-6}$-alkyl include methyl, ethyl, propyl, isopropyl, n-butyl, iso-butyl, sec-butyl, tert-butyl and pentyl. Particular alkyl groups include methyl, isopropyl and tert-butyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "carbonyl" denotes a —C(O)— group.

The term "cyano" denotes a —C≡N group.

The term "$C_{3-8}$-cycloalkyl" denotes monocyclic or polycyclic saturated or partially unsaturated, non-aromatic hydrocarbon. In some embodiments, unless otherwise described, cycloalkyl comprises 3 to 8 carbon atoms ($C_{3-8}$-cycloalkyl), 3 to 6 carbon atoms ($C_{3-6}$-cycloalkyl), or 3 to 5 carbon atoms ($C_{3-5}$-cycloalkyl). In some embodiments, cycloalkyl is a saturated monocyclic or polycyclic hydrocarbon. In other embodiments, cycloalkyl comprises one or more double bonds (e.g., cycloalkyl fused to an aryl or heteroaryl ring, or a non-aromatic monocyclic hydrocarbon comprising one or two double bonds). Polycyclic cycloalkyl groups may include spiro, fused, or bridged polycyclic moieties wherein each ring is a saturated or partially unsaturated, non-aromatic hydrocarbon. Examples for monocyclic cycloalkyl are cyclopropyl, cyclobutanyl, cyclopentyl, cyclohexyl, hydroxycyclobutyl, difluorocyclobutyl, difluoro-methyl-cyclobutyl, and methylcyclopropyl. Examples for bicyclic cycloalkyl are difluorospiroheptanyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, and hydroxycylopropylmethyl.

The term "halogen", "halide" and "halo" are used interchangeably herein and denote fluoro, chloro, bromo or iodo. Particular halogen is chloro.

The term "halo-$C_{1-6}$-alkoxy" denotes a $C_{1-6}$-alkoxy group wherein at least one of the hydrogen atoms of the $C_{1-6}$-alkoxy group has been replaced by the same or different halogen atoms. Particular examples are difluoromethoxy, trifluoromethoxy, difluoroethoxy and trifluoroethoxy.

The term "halo-$C_{1-6}$-alkyl" denotes a $C_{1-6}$-alkyl group wherein at least one of the hydrogen atoms of the $C_{1-6}$-alkyl group has been replaced by the same or different halogen atoms. Particular examples are fluoroethyl, difluoromethyl, trifluoromethyl, difluoroethyl, trifluoroethyl and 2-fluoro-1-(fluoromethyl)ethyl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having at least one ring atoms in common. The heterocycloalkyl group may be saturated or unsaturated, and unless otherwise specified, may comprise 5, 6, 7, 8 or 9 ring atoms, where ring atoms refer to the sum of carbon and heteroatoms in the one or more rings (e.g., be a 5-membered, 6-membered, 7-membered, 8-membered or 9-membered heterocycloalkyl). Heterocycloalkyl may include groups comprising 1 to 5 ring heteroatoms, 1 to 4 heteroatoms, 1 to 3 ring heteroatoms, 1 or 2 ring heteroatoms, or 1 ring heteroatom. In some embodiments, the heterocycloalkyl comprises one ring, two rings, three rings, four rings, or more, for example as a polycyclic fused system. In some embodiments, heterocycloalkyl comprising multiple rings includes spirocyclic systems in which one or more rings comprise one or more heteratoms. Examples for monocyclic heterocycloalkyl are oxetanyl, methyloxetanyl, tetrahydropyranyl, acetylpiperidyl, tetrahydrofuranyl.

The term "heterocycloalkylalkyl", denotes an alkyl group wherein at least one of the hydrogen atoms of the alkyl group is replaced by a heterocycloalkyl group. Examples of heterocycloalkylalkyl include oxetanylmethyl and (methyloxetanyl)methyl.

The term "hydroxy" denotes a —OH group.

The term "hydroxy-$C_{1-6}$-alkyl" denotes a $C_{1-6}$-alkyl group wherein one of the hydrogen atoms of the $C_{1-6}$-alkyl group is replaced by a hydroxy group. Particular examples are hydroxymethyl, hydroxyethyl and hydroxymethylpropyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides compounds according to formula (I) as described, wherein $R^1$ is selected from the groups consisting of
- i) H,
- ii) $C_{1-6}$-alkyl,
- iii) $C_{3-8}$-cycloalkyl
- iv) $C_{3-8}$-cycloalkylalkyl
- v) $C_{1-6}$-alkoxy
- vi) $C_{1-6}$-alkoxy-$C_{1-6}$-alkyl
- vii) Heterocycloalkyl
- viii) Heterocycloalkylalkyl
- ix) Substituted $C_{3-8}$-cycloalkyl
- x) Substituted $C_{3-8}$-cycloalkylalkyl
- xi) Substituted Heterocycloalkyl
- xii) Substituted Heterocycloalkylalkyl
- xiii) halo-$C_{1-6}$-alkyl
- xiv) hydroxy-$C_{1-6}$-alkyl wherein Substituted $C_{3-8}$-cycloalkyl or Subsisted Heterocycloalkyl are substituted with one or more substituents selected from H, $C_{1-6}$-alkyl, halogen, hydroxy, and $C_{1-6}$-carbonyl $R^2$ is selected from the group consisting of
- i) H,
- ii) halogen,
- iii) halo-$C_{1-6}$-alkyl
- iv) $C_{1-6}$-alkyl;
- v) cyano wherein at least one of $R^1$ and $R^2$ are other than H;

$R^3$ is selected from the groups consisting of
- i) H,
- ii) halogen, and n is 0 or 1.

or pharmaceutically acceptable salts.

A particular embodiment of the present invention provides compounds according to formula (I) as described herein, wherein $R^3$ is Halogen.

A further particular embodiment of the present invention provides compounds according to formula (I) as described herein, wherein $R^3$ is Cl.

Another further particular embodiment of the present invention provides compounds according to formula (I) as described herein, wherein $R^2$ is selected from the groups consisting of:
- i) H,
- ii) Cyano.

A particular embodiment of the present invention provides compounds according to formula (I) as described herein, wherein $R^1$ is selected from the groups consisting of
- i) H,
- ii) $C_{1-6}$-alkyl,
- iii) $C_{3-8}$-cycloalkyl
- iv) $C_{3-8}$-cycloalkylalkyl
- v) $C_{1-6}$-alkoxy
- vi) $C_{1-6}$-alkoxy-$C_{1-6}$-alkyl
- vii) Heterocycloalkyl
- viii) Heterocycloalkylalkyl
- ix) Substituted $C_{3-8}$-cycloalkyl
- x) Substituted $C_{3-8}$-cycloalkylalkyl
- xi) Substituted Heterocycloalkyl
- xii) Substituted Heterocycloalkylalkyl
- xiii) halo-$C_{1-6}$-alkyl
- xiv) hydroxy-$C_{1-6}$-alkyl wherein Substituted $C_{3-8}$-cycloalkyl or Substituted Heterocycloalkyl are substituted with one or more substituents selected from H, $C_{1-6}$-alkyl, halogen, hydroxy, and $C_{1-6}$-carbonyl, and "heterocycloalkyl" is a 4-6 atom ring system comprising one heteroatom selected from N and O.

A particular embodiment of the present invention provides compounds according to formula I as described herein, wherein $R^3$ is Cl, $R^2$ is H or cyano, and $R^1$ is selected from the groups consisting of i) H,
ii) $C_{1-6}$-alkyl,
iii) $C_{3-8}$-cycloalkyl
iv) $C_{3-8}$-cycloalkylalkyl
v) $C_{1-6}$-alkoxy
vi) $C_{1-6}$-alkoxy-$C_{1-6}$-alkyl
vii) Heterocycloalkyl
viii) Heterocycloalkylalkyl
ix) Substituted $C_{3-8}$-cycloalkyl
x) Substituted $C_{3-8}$-cycloalkylalkyl
xi) Substituted Heterocycloalkyl
xii) Substituted Heterocycloalkylalkyl
xiii) halo-$C_{1-6}$-alkyl
xiv) hydroxy-$C_{1-6}$-alkyl wherein Substituted $C_{3-8}$-cycloalkyl or Substituted Heterocycloalkyl are substituted with one or more substituents selected from H, $C_{1-6}$-alkyl, halogen, hydroxy, and $C_{1-6}$-carbonyl, and "heterocycloalkyl" is a 4-6 atom ring system comprising one heteroatom selected from N and O wherein at least one of $R^1$ and $R^2$ are other than H;
and n is 0 or 1.
or pharmaceutically acceptable salts.

Particular examples of compounds of formula (I) as described herein are selected from 2-((5-chloro-2,3-dihydro-1H-inden-2-yl)amino)-6-(oxetan-3-yl)-6,7-dihydro-5H-pyrrolo[3,4-d]pyrimidin-5-one;
2-((5-chloro-2,3-dihydro-1H-inden-2-yl)amino)-6-(3-methyloxetan-3-yl)-6,7-dihydro-5H-pyrrolo[3,4-d]pyrimidin-5-one;
(S)-6-chloro-2-((6-(3-methyloxetan-3-yl)-5-oxo-6,7-dihydro-5H-pyrrolo[3,4-d]pyrimidin-2-yl)amino)-2,3-dihydro-1H-indene-4-carbonitrile;
2-((5-chloro-2,3-dihydro-1H-inden-2-yl)amino)-6-(6,6-difluorospiro[3.3]heptan-2-yl)-6,7-dihydro-5H-pyrrolo[3,4-d]pyrimidin-5-one;
2-((5-chloro-2,3-dihydro-1H-inden-2-yl)amino)-6-(3,3-difluorocyclobutyl)-6,7-dihydro-5H-pyrrolo[3,4-d]pyrimidin-5-one;
(S)-6-chloro-2-((6-(3,3-difluoro-1-methylcyclobutyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(6,6-difluorospiro[3.3]heptan-2-yl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(3,3-difluorocyclobutyl)-5-oxo-6,7-dihydro-5H-pyrrolo[3,4-d]pyrimidin-2-yl)amino)-2,3-dihydro-1H-indene-4-carbonitrile;
(S)-6-chloro-2-((5-oxo-6-(tetrahydro-2H-pyran-4-yl)-6,7-dihydro-5H-pyrrolo[3,4-d]pyrimidin-2-yl)amino)-2,3-dihydro-1H-indene-4-carbonitrile;
(S)-6-chloro-2-((5-oxo-6-(2,2,2-trifluoroethyl)-6,7-dihydro-5H-pyrrolo[3,4-d]pyrimidin-2-yl)amino)-2,3-dihydro-1H-indene-4-carbonitrile;
(S,S) and (S,R)-6-chloro-2-((5-oxo-6-(tetrahydrofuran-3-yl)-6,7-dihydro-5H-pyrrolo[3,4-d]pyrimidin-2-yl)amino)-2,3-dihydro-1H-indene-4-carbonitrile;
(S)-6-chloro-2-((6-isopropyl-5-oxo-6,7-dihydro-5H-pyrrolo[3,4-d]pyrimidin-2-yl)amino)-2,3-dihydro-1H-indene-4-carbonitrile;
(S)-6-chloro-2-((6-cyclopropyl-5-oxo-6,7-dihydro-5H-pyrrolo[3,4-d]pyrimidin-2-yl)amino)-2,3-dihydro-1H-indene-4-carbonitrile;
(S)-6-chloro-2-((6-(oxetan-3-ylmethyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(1-methylcyclopropyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(oxetan-3-yl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(oxetan-3-yl)-5-oxo-5,6,7,8-tetrahydropyrido[4,3-d]pyrimidin-2-yl)amino)-2,3-dihydro-1H-indene-4-carbonitrile;
(S)-6-chloro-2-((6-(cyclopropylmethyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-((1r,3S)-3-hydroxycyclobutyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(2-methoxyethyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(2-hydroxy-2-methylpropyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-(2-fluoroethyl)-5-oxo-6,7-dihydro-5H-pyrrolo[3,4-d]pyrimidin-2-yl)amino)-2,3-dihydro-1H-indene-4-carbonitrile;
(S)-6-chloro-2-((6-methyl-5-oxo-6,7-dihydro-5H-pyrrolo[3,4-d]pyrimidin-2-yl)amino)-2,3-dihydro-1H-indene-4-carbonitrile;
(S)-6-chloro-2-((6-((1-hydroxycyclopropyl)methyl)-5-oxo-6,7-dihydro-5H-pyrrolo[3,4-d]pyrimidin-2-yl)amino)-2,3-dihydro-1H-indene-4-carbonitrile;
(S)-2-((6-(1-acetylpiperidin-4-yl)-5-oxo-6,7-dihydro-5H-pyrrolo[3,4-d]pyrimidin-2-yl)amino)-6-chloro-2,3-dihydro-1H-indene-4-carbonitrile;
(S)-6-chloro-2-((6-(1,3-difluoropropan-2-yl)-5-oxo-6,7-dihydro-5H-pyrrolo[3,4-d]pyrimidin-2-yl)amino)-2,3-dihydro-1H-indene-4-carbonitrile;
(S)-6-chloro-2-((5-oxo-5,6,7,8-tetrahydropyrido[4,3-d]pyrimidin-2-yl)amino)-2,3-dihydro-1H-indene-4-carbonitrile;
(S)-6-chloro-2-((6-((3-methyloxetan-3-yl)methyl)-5-oxo-6,7-dihydro-5H-pyrrolo[3,4-d]pyrimidin-2-yl)amino)-2,3-dihydro-1H-indene-4-carbonitrile;
(S)-6-chloro-2-((5-oxo-6-(tetrahydro-2H-pyran-4-yl)-5,6,7,8-tetrahydropyrido[4,3-d]pyrimidin-2-yl)amino)-2,3-dihydro-1H-indene-4-carbonitrile;
(S)-6-chloro-2-((6-isopropyl-5-oxo-5,6,7,8-tetrahydropyrido[4,3-d]pyrimidin-2-yl)amino)-2,3-dihydro-1H-indene-4-carbonitrile;
(S)-6-chloro-2-((6-(cyclopropylmethyl)-5-oxo-5,6,7,8-tetrahydropyrido[4,3-d]pyrimidin-2-yl)amino)-2,3-dihydro-1H-indene-4-carbonitrile;
(S,S) and (S,R)6-chloro-2-((5-oxo-6-(tetrahydrofuran-3-yl)-5,6,7,8-tetrahydropyrido[4,3-d]pyrimidin-2-yl)amino)-2,3-dihydro-1H-indene-4-carbonitrile;
(S)-6-chloro-2-((6-ethyl-5-oxo-6,7-dihydro-5H-pyrrolo[3,4-d]pyrimidin-2-yl)amino)-2,3-dihydro-1H-indene-4-carbonitrile;
(S)-6-chloro-2-((6-ethyl-5-oxo-5,6,7,8-tetrahydropyrido[4,3-d]pyrimidin-2-yl)amino)-2,3-dihydro-1H-indene-4-carbonitrile;

(S)-6-chloro-2-((5-oxo-6,7-dihydro-5H-pyrrolo[3,4-d]pyrimidin-2-yl)amino)-2,3-dihydro-1H-indene-4-carbonitrile;

(S)-6-chloro-2-((5-oxo-6-(2,2,2-trifluoroethyl)-5,6,7,8-tetrahydropyrido[4,3-d]pyrimidin-2-yl)amino)-2,3-dihydro-1H-indene-4-carbonitrile;

and pharmaceutically acceptable salts thereof.

Processes for the manufacture of compounds of formula (I) as described herein are an object of the invention.

The present compounds of formula I and their pharmaceutically acceptable salts can be prepared by methods known in the art, for example, by the process described below, which process comprises reacting a compound of formula

II

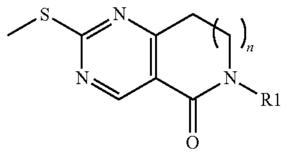

with an oxidant like 3-chloroperbenzoic acid to transform II into its corresponding methyl sulfone derivative which is then reacting with a compound of formula

III

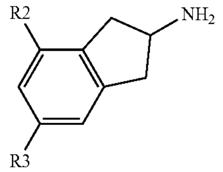

in the presence of a base like N,N-diisopropylethylamine to provide a compound of formula

I

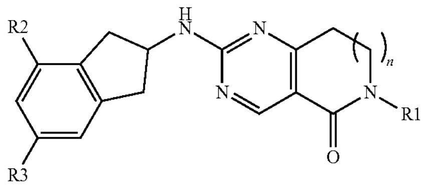

wherein the substituents are as defined above.

The compounds of formula I may be prepared in accordance with the process variant described above and with the following schemes 1-3. The starting materials are commercially available or may be prepared in accordance with known methods.

Scheme 1

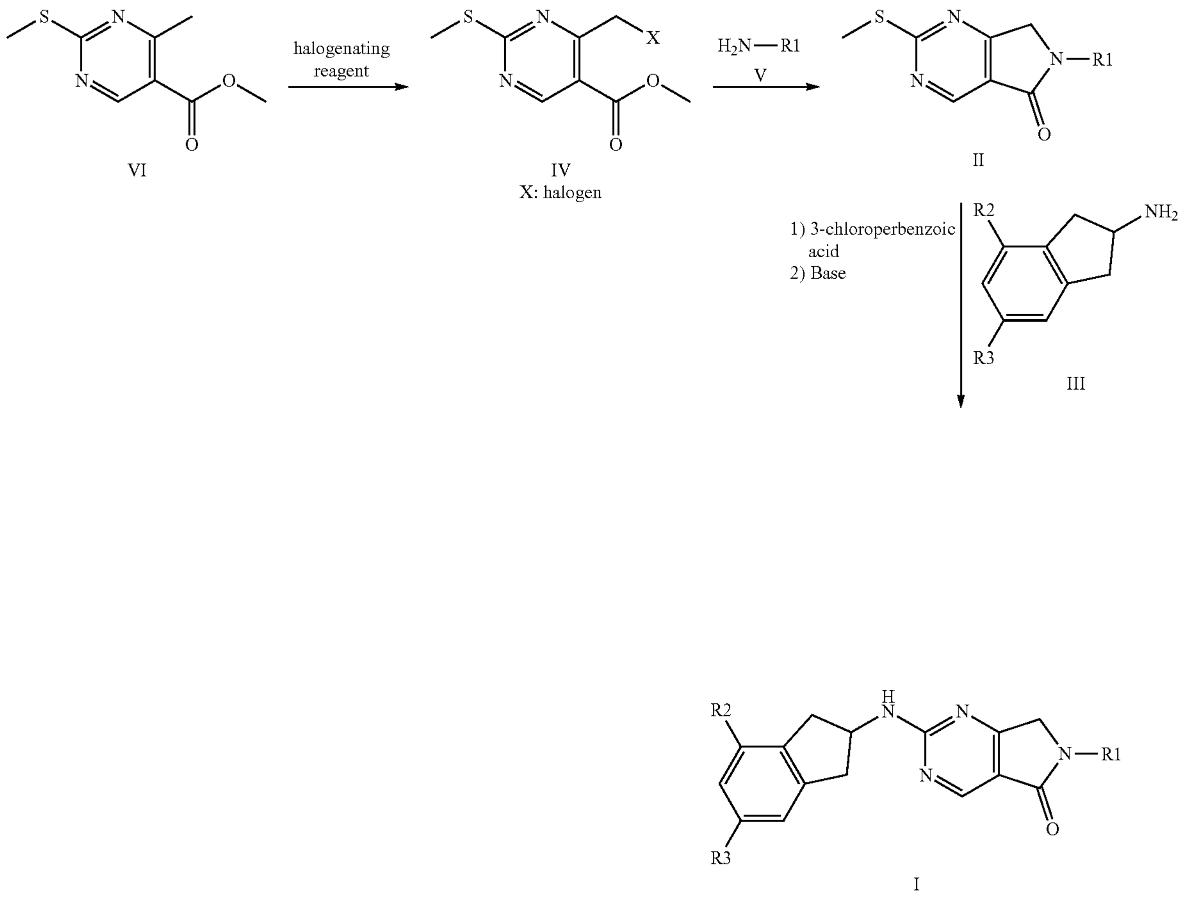

Compounds of general formula I wherein n is 0 can be prepared by reacting a thiomethyl derivative II with an oxidant like 3-chloroperbenzoic acid to transform II into its corresponding methyl sulfone derivative which is then reacted with the amine derivative III. The thiomethyl derivative of formula II can be prepared by reaction of an amine V with an halo-methyl derivative of formula IV which itself can be prepared from VI in the presence of an halogenating agent like bromine.

Scheme 2

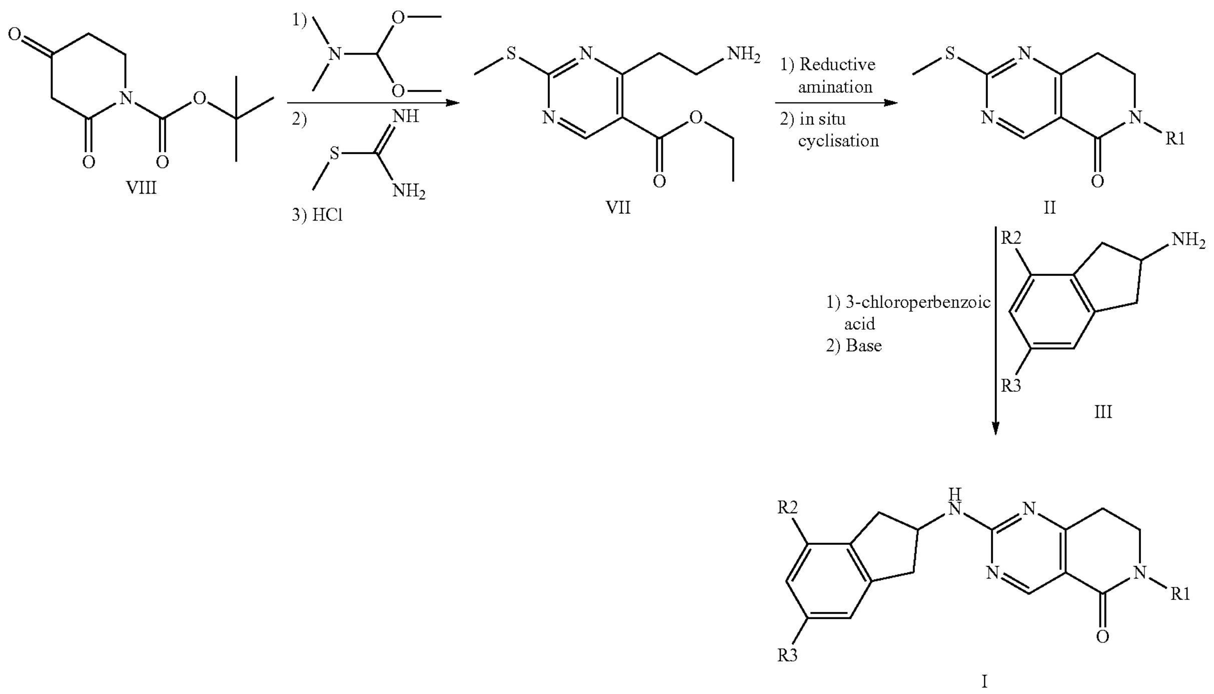

Compounds of general formula I wherein n is 1 can be prepared by reacting a thiomethyl derivative II with an oxidant like 3-chloroperbenzoic acid to transform II into its corresponding methyl sulfone derivative which is then reacted with the amine derivative III. The thiomethyl derivative of formula II can be prepared by reductive amination of an aldehyde or ketone with an amine VII in the presence of a reducing agent like sodium triacetoxyborohydride followed by an in situ cyclisation. VII can be prepared from tert-butyl 2,4-dioxopiperidine-1-carboxylate VIII in the presence of 1,1-dimethoxy-N,N-dimethylmethanamine and 2-methylisothiourea in a solvent like ethanol followed by a treatment with an acid like HCl.

Scheme 3

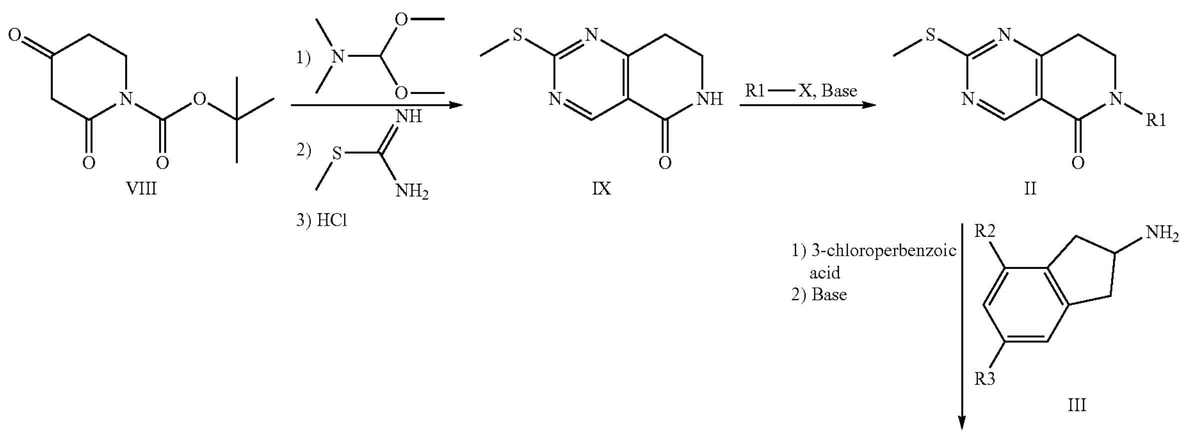

-continued

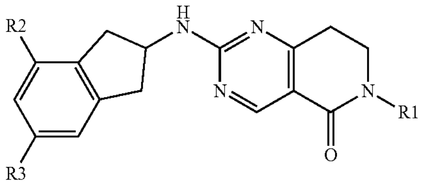

I

Alternatively, compounds of general formula I wherein n is 1 can be prepared by reacting a thiomethyl derivative II with an oxidant like 3-chloroperbenzoic acid to transform II into its corresponding methyl sulfone derivative which is then reacted with the amine derivative III. The thiomethyl derivative of formula II can be prepared by alkylation of cyclic amide IX in the presence of an alkylating agent R1-X wherein X is an halogen or an alkyl-trifluoromethane-sulfonate and a base like diisopropylethylamine. IX can be prepared from tert-butyl 2,4-dioxopiperidine-1-carboxylate VIII in the presence of 1,1-dimethoxy-N,N-dimethylmeth-anamine and 2-methylisothiourea in a solvent like ethanol followed by a treatment with an acid like HCl.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

Also an embodiment of the present invention provides compounds of formula (I) as described herein, when manufactured according to any one of the described processes.

Assay Procedures

Production of Human Full Length ATX, with and without His Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltered through a 0.2 μm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

To identify inhibitors of the human Autotaxin (ATX) enzyme an in-vitro biochemical profiling assay has been developed using lysophosphatidylcholine (LPC) as substrate and recombinant enzyme. ATX activity is assayed via a coupled enzyme format where choline produced from LPC hydrolysis is converted to hydrogen peroxide by choline oxidase (CO). Hydrogen peroxide is in turn used as a co-substrate by horseradish peroxidase (HRP) to oxidise Amplex Red® and generate the red-fluorescent product, Resorufin.

Materials/Reagents 500 mM Tris-HCl pH 8.0; 1M NaCl; 250 mM $CaCl_2$; 250 mM KCl; 250 mM $MgCl_2$; 10% Triton X-100 in $H_2O$.

Assay Buffer 50 mM Tris-HCl (pH 8.0); 120 mM NaCl; 20 mM $CaCl_2$; 5 mM KCl; 1 mM $MgCl_2$; 0.01% Triton X-100, sterile-filtered and stored at 4° C.

Reagent Dilution Buffer 50 mM Tris-HCl (pH 8.0); 150 mM NaCl human Autotaxin (hATX): 0.97 mg/ml (9.718 μM) Molecular weight 99817. Working solution of 1.5 μM used in this assay.

100 mM 18:1 LPC dissolved in reagent dilution-buffer.

500 U/ml Choline Oxidase in reagent dilution buffer.

2540 U/ml Horseradish Peroxidase, in reagent dilution buffer (10.95 mg/ml).

20 mM Amplex Red (10-Acetyl-3,7-dihydroxy-phenoxazin) in DMSO.

Reaction Plate

Black, 384-well plate, black with clear bottom, non-treated surface.

Test compounds are received pre-diluted in DMSO as an 11-point concentration-response (0.5 mM highest concentration; 1 in 3.162 dilution). Test compounds are pre-diluted 1:1 (10 μL compound+10 μL assay buffer) in a 96-well conical bottomed plate prior to use.

Procedure

ATX is diluted to 2.2 nM in assay buffer. Choline oxidase and horseradish peroxidase are diluted to 7.3 U/ml and 14.7 U/ml, respectively. 18:1 LPC and Amplex Red® are diluted to 110 μM and 183.3 μM, respectively (solution protected from light). 2.2 μL of compound pre-dilution or 50% DMSO is added to the reaction plate followed by 25 μL of ATX or assay buffer (negative control). Assay plate is mixed and incubated at room temperature for 10 mins. 15 μL of choline oxidase/horseradish peroxidase is then added. To initiate the reaction 15 μL of LPC 18:1/Amplex Red is added. Assay plate is mixed and incubated at room temperature in the dark. Fluorescence is measured at 5 mins (for background subtraction) and 90 mins.

Final Assay Concentrations:

hATX: 1 nM

18:1 LPC: 30 μM

Choline Oxidase: 2 U/ml

Horse Radish Peroxidase: 4 U/ml

Amplex Red®: 50 μM

DMSO: 2%

Fluorescence at 5-minutes is subtracted from the 90-minute end point data and normalized with respect to the positive control. $IC_{50}$ values are calculated.

Results in the enzymatic ATX inhibition assay are provided for compounds of formula (I).

TABLE 1

| Example | ATX IC50 [μM] |
|---|---|
| 1 | 0.15 |
| 2 | 0.183 |
| 3 | 0.005 |
| 4 | 0.042 |
| 5 | 0.049 |
| 6 | 0.004 |
| 7 | 0.003 |
| 8 | 0.003 |
| 9 | 0.005 |
| 10 | 0.002 |
| 11 | 0.006 |
| 12 | 0.003 |
| 13 | 0.002 |
| 14 | 0.003 |
| 15 | 0.002 |
| 16 | 0.004 |
| 17 | 0.003 |
| 18 | 0.003 |
| 19 | 0.005 |
| 20 | 0.005 |
| 21 | 0.005 |
| 22 | 0.002 |
| 23 | 0.003 |
| 24 | 0.009 |
| 25 | 0.006 |
| 26 | 0.004 |
| 27 | 0.003 |
| 28 | 0.006 |
| 29 | 0.004 |
| 30 | 0.002 |
| 31 | 0.002 |
| 32 | 0.004 |
| 33 | 0.002 |
| 34 | 0.003 |
| 35 | 0.002 |
| 36 | 0.003 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Intermediates A

Intermediate A1: 5-chloro-2,3-dihydro-1H-inden-2-amine hydrochloride

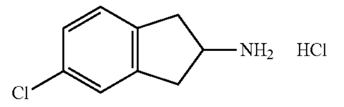 [SMILES: NC1Cc2ccc(Cl)cc2C1 ; Cl]

Intermediate A1 is commercial (CAS: 73536-86-4)

Intermediate A2: (S)-6-chloro-4-cyano-2,3-dihydro-1H-inden-2-aminium chloride

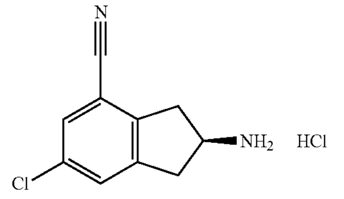 [SMILES: N#Cc1cc(Cl)cc2c1C[C@@H](N)C2 ; Cl]

Step 1: 4-(4,4,5,5-tetramethyl-1,3,2-dioxaborolan-2-yl)-2,3-dihydro-1H-inden-2-yl)carbamate

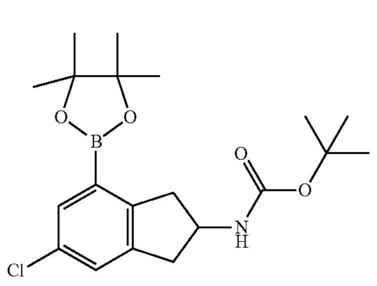 [SMILES: CC(C)(C)OC(=O)NC1Cc2cc(Cl)cc(B3OC(C)(C)C(C)(C)O3)c2C1]

4,4,4',4',5,5,5',5'-Octamethyl-2,2'-bi(1,3,2-dioxaborolane) (2.42 g, 9.34 mmol), (1,5-cyclooctadiene)(methoxy) iridium (I) dimer (309 mg, 467 µmol), tert-butyl (5-chloro-2,3-dihydro-1H-inden-2-yl)carbamate (2.50 g, 9.34 mmol, CAS: 1934835-81-0) and 3,4,7,8-tetramethyl-1,10-phenanthroline (221 mg, 934 µmol) were combined in a microwave vial (dried using high vacuum and flushed with Argon) and were suspended in dry THF (10 ml). On mixing these reagents, the suspension turned dark green. Argon was bubbled through the suspension for 10 min. The reaction mixture was heated to 80° C. and stirred for 15 h (turned dark violet). The reaction mixture was filtered through sintered glass and concentrated in vacuo. The crude material was purified by flash chromatography over silica gel using a gradient ethylacetate/heptane 0-30% to provide the title compound as an off-white solid (2.30 g, 63% yield). MS (ESI): m/z=294.2 $[M-Boc+H]^+$

Step 2: Tert-butyl (6-chloro-4-hydroxy-2,3-dihydro-1H-inden-2-yl)carbamate

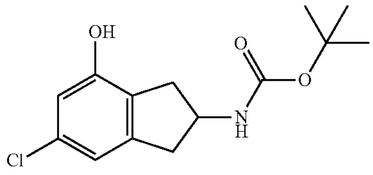 [SMILES: CC(C)(C)OC(=O)NC1Cc2cc(Cl)cc(O)c2C1]

4-(4,4,5,5-tetramethyl-1,3,2-dioxaborolan-2-yl)-2,3-dihydro-1H-inden-2-yl)carbamate (850 mg, 1.84 mmol) was dissolved in THF (5.56 ml) and water (556 µl) and sodium perborate monohydrate (549 mg, 5.51 mmol) was added. The reaction was stirred at rt for 18 hours. The solvent was evaporated and the residue was taken up in water and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a off-white solid (220 mg, 42% yield). MS (ESI): m/z=282.2 $[M-H]^+$

Step 3: 2-((tert-butoxycarbonyl)amino)-6-chloro-2,3-dihydro-1H-inden-4-yl trifluoromethanesulfonate

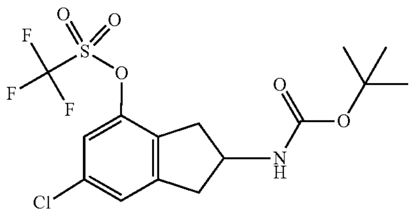 [SMILES: CC(C)(C)OC(=O)NC1Cc2cc(Cl)cc(OS(=O)(=O)C(F)(F)F)c2C1]

Tert-butyl (6-chloro-4-hydroxy-2,3-dihydro-1H-inden-2-yl)carbamate (50 mg, 176 µmol) was dissolved in dry DCM (705 µl) and triethylamine (19.6 mg, 27 µl, 194 µmol) was added. To this stirred solution, 1,1,1-trifluoro-N-phenyl-N-((trifluoromethyl)sulfonyl)methanesulfonamide (69.2 mg, 194 µmol) was added. The reaction was stirred at rt for 3 hours, poured into water and extracted with EtOAc. The layers were separated and the aqueous layer was extracted twice with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a white solid (42 mg, 57% yield). MS (ESI): m/z=414.1 $[M-H]^+$ Step 4: tert-butyl (6-chloro-4-cyano-2,3-dihydro-1H-inden-2-yl)carbamate

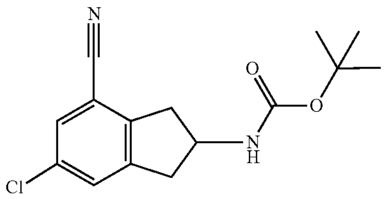 [SMILES: CC(C)(C)OC(=O)NC1Cc2cc(Cl)cc(C#N)c2C1]

2-((tert-butoxycarbonyl)amino)-6-chloro-2,3-dihydro-1H-inden-4-yl trifluoromethanesulfonate (60 mg, 144 μmol), zinc cyanide (9.32 mg, 79.4 μmol) and tetrakis (triphenylphosphine) palladium (0) (16.7 mg, 14.4 μmol) were dissolved in dry DMF (721 μl) and Argon was bubbled through the reaction for 5 minutes. Following, the reaction was heated to 110° C. for 2 hours. The reaction was poured into LiCl 10% and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ethylacetate/heptane 0-50% to provide the title compound as a white solid (24 mg, 57% yield).

MS (ESI): m/z=237.1 $[M-tBu]^+$

Step 5: (S)-tert-butyl (6-chloro-4-cyano-2,3-dihydro-1H-inden-2-yl)carbamate

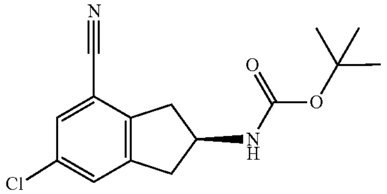 [SMILES: CC(C)(C)OC(=O)N[C@H]1Cc2cc(Cl)cc(C#N)c2C1]

tert-butyl (6-chloro-4-cyano-2,3-dihydro-1H-inden-2-yl) carbamate (65 mg, 222 μmol) was separated on a chiral column (OZ-H, 12 nm, 5 μm, 250×4.6 mm) on SFC condition to provide the title compound as a white solid (32 mg, 49.2% yield, 96% ee, second eluting enantiomer, retention time: 6.6 min.). MS (ESI) m/z: 237.1 $[M-tBu]^+$ Step 6: (S)-6-chloro-4-cyano-2,3-dihydro-1H-inden-2-aminium chloride

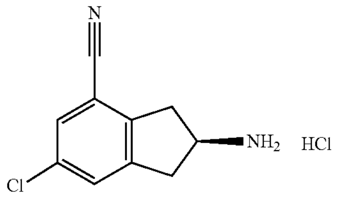 [SMILES: N#Cc1cc(Cl)cc2c1C[C@@H](N)C2 ; Cl]

A solution of (S)-tert-butyl-(6-chloro-4-cyano-2,3-dihydro-1H-inden-2-yl)carbamate; (300 mg, 1.02 mmol) and HCl 4 M in dioxane (3.84 ml, 15.4 mmol) in dioxane (2 ml) was stirred at rt for 15 h. The resulting suspension was concentrated in vacuo to provide the title compound (237 mg, 100% yield) as a white solid. MS (ESI): m/z=193.1 [M+H]+.

Intermediates B

Intermediate B1: methyl 4-(bromomethyl)-2-(methylthio)pyrimidine-5-carboxylate

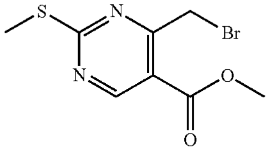

To a solution of methyl 4-methyl-2-(methylthio)pyrimidine-5-carboxylate (1.00 g, 4.79 mmol, CAS: 166392-24-1) in acetic acid (10 ml) was added bromine (774 mg, 249 μl, 4.79 mmol). The reaction mixture was heated to 60° C. and stirred for 1 h. Bromine (232 mg, 74.6 μl, 1.44 mmol) was added again and the stirring was continued at 60° C. for 1 h. The reaction mixture was concentrated in vacuo, poured into water and extracted twice with EtOAc. The combined organic layers were dried over sodium sulfate and concentrated in vacuo. The crude material was purified by flash chromatography over silica gel using a gradient ethylacetate/heptane 0-50% to provide the title compound as a light yellow viscous oil (822 mg, 54% yield). MS (ESI): m/z=277.0 $[M+H]^+$ Intermediate B2: ethyl 4-(2-aminoethyl)-2-(methylthio)pyrimidine-5-carboxylate hydrochloride

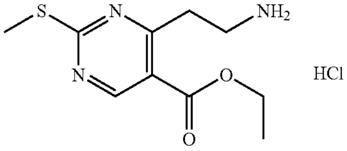 [SMILES: CCOC(=O)c1cnc(SC)nc1CCN ; Cl]

Step 1: ethyl 4-(2-((tert-butoxycarbonyl)amino)ethyl)-2-(methylthio)pyrimidine-5-carboxylate

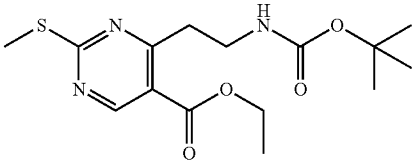 [SMILES: CCOC(=O)c1cnc(SC)nc1CCNC(=O)OC(C)(C)C]

A suspension of tert-butyl 2,4-dioxopiperidine-1-carboxylate (2.00 g, 9.19 mmol) and 1,1-dimethoxy-N,N-dimethylmethanamine (1.24 g, 1.38 ml, 10.1 mmol) in toluene (20 ml) was stirred at rt for 1 h. The resulting yellow solution was concentrated in vacuo and diluted with EtOH (40 ml). Methyl carbamimidothioate hemisulfate (1.44 g, 5.06 mmol)

and potassium carbonate (1.92 g, 13.8 mmol) were added. The reaction mixture was stirred at rt for 20 h, poured into water/brine and extracted twice with EtOAc. The combined organic layers were dried over sodium sulfate and concentrated in vacuo. The crude material was purified by flash chromatography over silica gel using a gradient ethylacetate/heptane 0-50% to provide the title compound as a white solid (2.36 g, 75% yield). MS (ESI): m/z=342.2 $[M+H]^+$ Step 2: ethyl 4-(2-aminoethyl)-2-(methylthio)pyrimidine-5-carboxylate hydrochloride

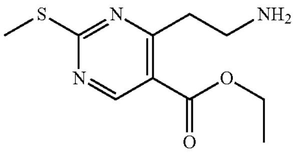

HCl

The title compound was prepared from ethyl 4-(2-((tert-butoxycarbonyl)amino)ethyl)-2-(methylthio)pyrimidine-5-carboxylate following procedure described for intermediate A2, step 6 (100% yield, white solid). MS (ESI): m/z=242.2 $[M+H]^+$ Intermediate B3: tert-butyl 2-(methylthio)-5-oxo-7,8-dihydropyrido[4,3-d]pyrimidine-6(5H)-carboxylate

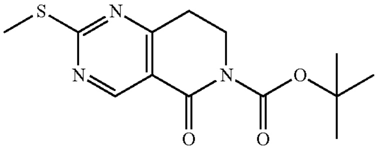 [SMILES: CSc1ncc2c(n1)CCN(C(=O)OC(C)(C)C)C2=O]

A suspension of tert-butyl 2,4-dioxopiperidine-1-carboxylate (500 mg, 2.3 mmol) and 1,1-dimethoxy-N,N-dimethylmethanamine (311 mg, 346 μl, 2.53 mmol) in toluene (5 ml) was stirred at rt for 1 h. The resulting yellow solution was concentrated in vacuo and diluted with EtOH (10 ml). Methyl carbamimidothioate hemisulfate (359 mg, 1.26 mmol) and potassium carbonate (481 mg, 3.45 mmol) were added. The reaction mixture was stirred at rt for 4 h, poured into water and extracted twice with EtOAc. The combined organic layers were dried over sodium sulfate and concentrated in vacuo. The crude material was purified by flash chromatography over silica gel using a gradient ethylacetate/heptane 0-50% to provide the title compound as a white solid (317 mg, 47% yield). MS (ESI): m/z=296.2 $[M+H]^+$

Intermediates C

Intermediate C1: 2-(methylthio)-6-(oxetan-3-yl)-6,7-dihydro-5H-pyrrolo[3,4-d]pyrimidin-5-one

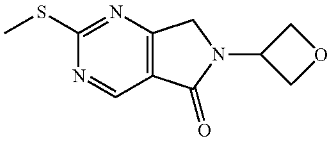 [SMILES: CSc1ncc2c(n1)CN(C1COC1)C2=O]

A solution of methyl 4-(bromomethyl)-2-(methylthio)pyrimidine-5-carboxylate (413 mg, 1.3 mmol, intermediate B1), oxetan-3-amine (484 mg, 464 μl, 6.48 mmol) and N,N-diisopropylethylmaine (342 mg, 452 μl, 2.59 mmol) in DMA (6 ml) was stirred at rt for 2 h. The reaction mixture was heated to 65° C. and stirred for 3 h. The reaction mixture was poured into water and extracted twice with EtOAc. The combined organic layers were dried over sodium sulfate and concentrated in vacuo. The crude material was purified by flash chromatography over silica gel using a gradient ethylacetate/heptane 0-100% to provide the title compound as an off-white solid (158 mg, 51% yield). MS (ESI): m/z=238.1 $[M+H]^+$ The following intermediates C2-24 were prepared in analogy to intermediate C1 from the indicated commercial amine building block and methyl 4-(bromomethyl)-2-(methylthio)pyrimidine-5-carboxylate (intermediate B1)

| Int. | Structure | name | Amine Building block | MS (ESI): m/z; $[M + H]^+$ |
|---|---|---|---|---|
| C2 | 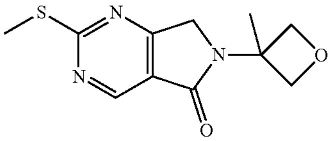 [SMILES: CSc1ncc2c(n1)CN(C1(C)COC1)C2=O] | 6-(3-methyloxetan-3-yl)-2-(methylthio)-6,7-dihydro-5H-pyrrolo[3,4-d]pyrimidin-5-one | 3-methyloxetan-3-amine | 252.1 |
| C3 | 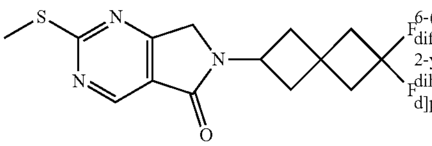 | 6-(6,6-difluorospiro[3.3]heptan-2-yl)-2-(methylthio)-6,7-dihydro-5H-pyrrolo [3,4-d]pyrimidin-5-one | 6,6-difluoro-spiro[3.3] heptan-2-amine hydrochloride | 312.2 |
| C4 | 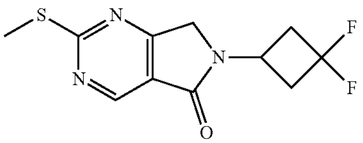 [SMILES: CSc1ncc2c(n1)CN(C1CC(F)(F)C1)C2=O] | 6-(3,3-difluorocyclobutyl)-2-(methylthio)-6,7-dihydro-5H-pyrrolo[3,4-d]pyrimidin-5-one | 3,3-difluoro-cyclobutan-1-amine hydro-chloride | 272.2 |

-continued

| Int. | Structure | name | Amine Building block | MS (ESI): m/z; [M + H]$^+$ |
|---|---|---|---|---|
| C5 | 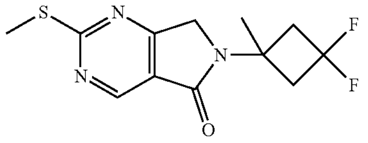 [SMILES: CSc1ncc2c(n1)CN(C1(C)CC(F)(F)C1)C2=O] | 6-(3,3-difluoro-1-methylcyclobutyl)-2-(methylthio)-6,7-dihydro-5H-pyrrolo[3,4-d] pyrimidin-5-one | 3,3-difluoro-1-methyl-cyclobutan-1-amine hydro-chloride | 286.2 |
| C6 | 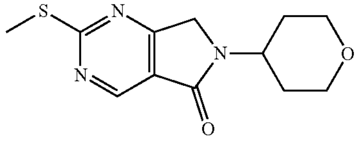 [SMILES: CSc1ncc2c(n1)CN(C1CCOCC1)C2=O] | 2-(methylthio)-6-(tetrahydro-2H-pyran-4-yl)-6,7-dihydro-5H-pyrrolo[3,4-d]pyrimidin-5-one | tetrahydro-2H-pyran-4-amine | 266.2 |
| C7 | 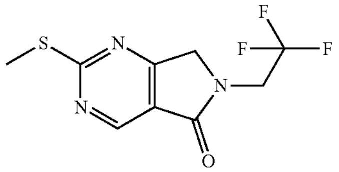 [SMILES: CSc1ncc2c(n1)CN(CC(F)(F)F)C2=O] | 2-(methylthio)-6-(2,2,2-trifluoroethyl)-6,7-dihydro-5H-pyrrolo[3,4-d] pyrimidin-5-one | 2,2,2-trifluoro-ethan-1-amine | 264.1 |
| C8 | 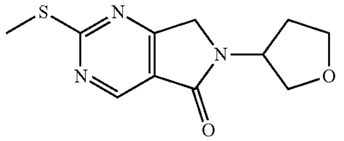 [SMILES: CSc1ncc2c(n1)CN(C1CCOC1)C2=O] | 2-(methylthio)-6-(tetrahydrofuran-3-yl)-6,7-dihydro-5H-pyrrolo[3,4-d]pyrimidin-5-one | tetrahydro furan-3-amine | 252.2 |
| C9 | 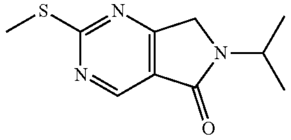 | 6-isopropyl-2-(methylthio)-6,7-dihydro-5H-pyrrolo[3,4-d]pyrimidin-5-one | isopropyl-amine | 224.1 |
| C10 | 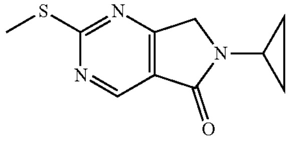 | 6-cyclopropyl-2-(methylthio)-6,7-dihydro-5H-pyrrolo[3,4-d]pyrimidin-5-one | cyclopropyl-amine | 222.1 |
| C11 | 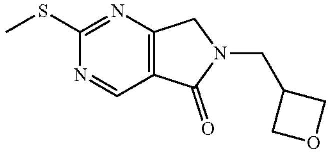 [SMILES: CSc1ncc2c(n1)CN(CC1COC1)C2=O] | 2-(methylthio)-6-(oxetan-3-ylmethyl)-6,7-dihydro-5H-pyrrolo[3,4-d]pyrimidin-5-one | oxetan-3-ylmethan-amine | 252.1 |
| C12 | 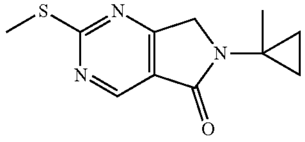 [SMILES: CSc1ncc2c(n1)CN(C1(C)CC1)C2=O] | 6-(1-methylcyclopropyl)-2-(methylthio)-6,7-dihydro-5H-pyrrolo[3,4-d]pyrimidin-5-one | 1-methylcy-clopropan-l-amine | 236.2 |
| C13 | 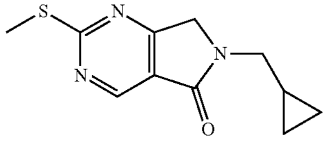 [SMILES: CSc1ncc2c(n1)CN(CC1CC1)C2=O] | 6-(1-methylcyclopropyl)-2-(methylthio)-6,7-dihydro-5H-pyrrolo[3,4-d]pyrimidin-5-one | 1-methylcy-clopropan-l-amine | 236.2 |

-continued

| Int. | Structure | name | Amine Building block | MS (ESI): m/z; [M + H]$^+$ |
|---|---|---|---|---|
| C14 | 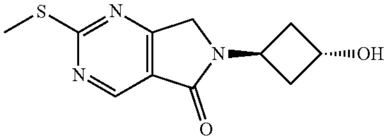 [SMILES: CSc1ncc2c(n1)CN([C@H]1C[C@H](O)C1)C2=O] | 6(trans-3-hydroxycyclobutyl)-2-(methylthio)-6,7-dihydro-5H-pyrrolo[3,4-d]pyrimidin-5-one | trans-3-aminocyclo-butan-1-ol hydrochlor-ide | 252.1 |
| C15 | 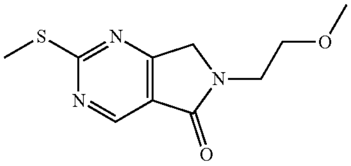 | 6-(2-methoxyethyl)-2-(methylthio)-6,7-dihydro-5H-pyrrolo[3,4-d]pyrimidin-5-one | 2-methoxy-ethan-1-amine | 240.1 |
| C16 | 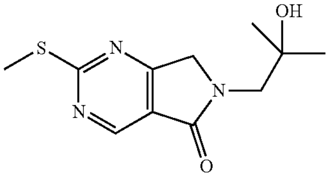 [SMILES: CSc1ncc2c(n1)CN(CC(C)(C)O)C2=O] | 6-(2-hydroxy-2-methylpropyl)-2-(methylthio)-6,7-dihydro-5H-pyrrolo[3,4-d]pyrimidin-5-one | 1-amino-2-methylprop-an-2-ol | 254.1 |
| C17 | 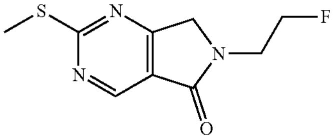 | 6-(2-fluoroethyl)-2-(methylthio)-6,7-dihydro-5H-pyrrolo[3,4-d]pyrimidin-5-one | 2-fluoroethan-1-amine hydrochlor-ide | 228.1 |
| C18 | 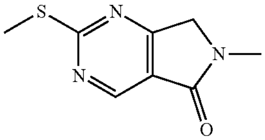 | 6-methyl-2-(methylthio)-6,7-dihydro-5H-pyrrolo[3,4-d]pyrimidin-5-one | methan-amine hydrochlor-ide | 196.1 |
| C19 | 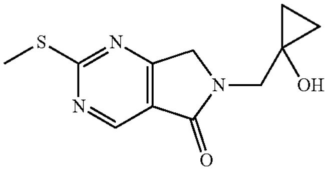 [SMILES: CSc1ncc2c(n1)CN(CC1(O)CC1)C2=O] | 6-((l-hydroxycyclopropyl)meth-yl)-2-(methylthio)-6,7-dihydro-5H-pyrrolo[3,4-d]pyrimidin-5-one | 1-(aminometh-yl)cyclo-propan-1-ol | 252.1 |
| C20 | 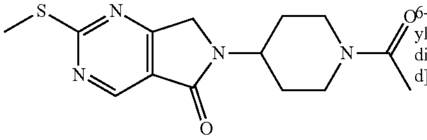 | 6-(1-acetylpiperidin-4-yl)-2-(methylthio)-6,7-dihydro-5H-pyrrolo[3,4-d]pyrimidin-5-one | l-(4-aminopip-eridin-1-yl)ethan-l-one | 307.1 |
| C21 | 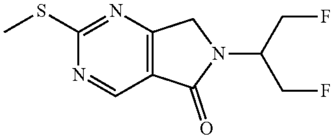 [SMILES: CSc1ncc2c(n1)CN(C(CF)CF)C2=O] | 6-(l,3-difluoropropan-2-yl)-2-(methylthio)-6,7-dihydro-5H-pyrrolo[3,4-d]pyrimidin-5-one | 1,3-difluoro-propan-2-amine | 260.1 |
| C22 | 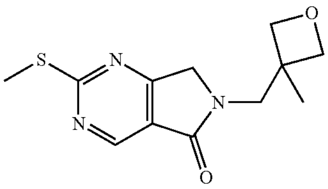 [SMILES: CSc1ncc2c(n1)CN(CC1(C)COC1)C2=O] | 6-((3-methyloxetan-3-yl)methyl)-2-(methylthio)-6,7-dihydro-5H-pyrrolo[3,4-d]pyrimidin-5-one | (3-methylox-etan-3-yl)methan amine | 266.1 |

-continued

| Int. | Structure | name | Amine Building block | MS (ESI): m/z; [M + H]$^+$ |
|---|---|---|---|---|
| C23 | 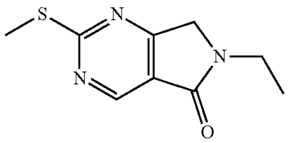 | 6-ethyl-2-(methylthio)-6,7-dihydro-5H-pyrrolo[3,4-d]pyrimidin-5-one | ethylamine | 210.1 |
| C24 | 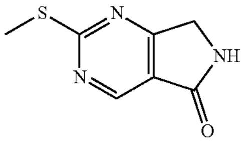 | 2-(methylthio)-6,7-dihydro-5H-pyrrolo[3,4-d]pyrimidin-5-one | ammonia | 182 |

Intermediate C25: 2-(methylthio)-6-(oxetan-3-yl)-7,8-dihydropyrido[4,3-d]pyrimidin-5(6H)-one

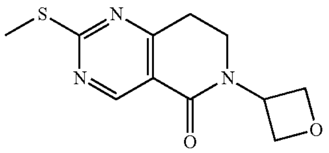 [SMILES: CSc1ncc2c(n1)CCN(C1COC1)C2=O]

To a stirred suspension of ethyl 4-(2-aminoethyl)-2-(methylthio)pyrimidine-5-carboxylate hydrochloride (140 mg, 504 μmol, intermediate B2) and oxetan-3-one (74.1 mg, 65.9 μl, 1.01 mmol) in 1,2-dichloroethane (4 ml) were added acetic acid (60.5 mg, 57.7 μl, 1.01 mmol) and sodium triacetoxyborohydride (320 mg, 1.51 mmol). The reaction mixture was stirred at rt for 20 h. The resulting cloudy solution was quenched with EtOH (140 μl). N,N-diisopropylamine (266 mg, 352 μl, 2.02 mmol) was added. The stirring was continued at rt for 2 h and at 70° C. for 2 h. The reaction mixture was poured into a saturated solution of sodium carbonate and extracted twice with dichloromethane. The combined organic layers were dried over sodium sulfate and concentrated in vacuo. The crude material was purified by flash chromatography over silica gel using a gradient ethylacetate/heptane 0-100% to provide the title compound as a white solid (45 mg, 36% yield). MS (ESI): m/z=252.1 [M+H]$^+$ The following intermediates C26-30 were prepared in analogy to intermediate C25 from the indicated commercial aldehyde or ketone building block and ethyl 4-(2-aminoethyl)-2-(methylthio)pyrimidine-5-carboxylate hydrochloride (intermediate B2)

| Int. | Structure | name | Amine Building block | MS (ESI): m/z; [M + H]$^+$ |
|---|---|---|---|---|
| C26 | 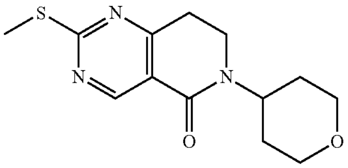 [SMILES: CSc1ncc2c(n1)CCN(C1CCOCC1)C2=O] | 2-(methylthio)-6-(tetrahydro-2H-pyran-4-yl)-7,8-dihydropyrido[4,3-d]pyrimidin-5(6H)-one | tetrahydro-4H-pyran-4-one | 280.1 |
| C27 | 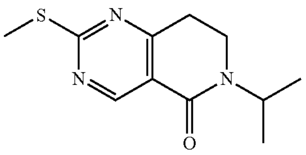 [SMILES: CSc1ncc2c(n1)CCN(C(C)C)C2=O] | 6-isopropyl-2-(methylthio)-7,8-dihydropyrido[4,3-d]pyrimidin-5(6H)-one | acetone | 238.1 |
| C28 | 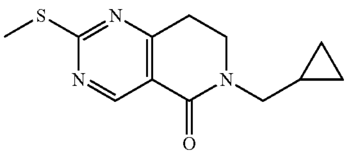 [SMILES: CSc1ncc2c(n1)CCN(CC1CC1)C2=O] | 6-(cyclopropylmethyl)-2-(methylthio)-7,8-dihydropyrido[4,3-d]pyrimidin-5(6H)-one | cyclopropanecarbaldehyde | 250.1 |

-continued

| Int. | Structure | name | Amine Building block | MS (ESI): m/z; [M + H]$^+$ |
|---|---|---|---|---|
| C29 | 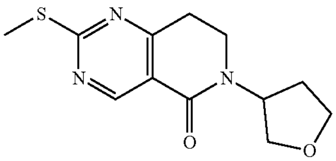 [SMILES: CSc1ncc2c(n1)CCN(C1CCOC1)C2=O] | 2-(methylthio)-6-(tetrahydrofuran-3-yl)-7,8-dihydropyrido[4,3-d]pyrimidin-5(6H)-one | dihydro-furan-3(2H)-one | 266.1 |
| C30 | 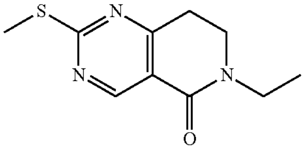 | 6-ethyl-2-(methylthio)-7,8-dihydropyrido[4,3-d]pyrimidin-5(6H)-one | acetalde-hyde | 224.1 |

Intermediate C31: 2-(methylthio)-7,8-dihydropyrido[4,3-d]pyrimidin-5(6H)-one

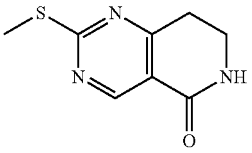

The title compound was prepared from tert-butyl 2-(methylthio)-5-oxo-7,8-dihydropyrido[4,3-d]pyrimidine-6(5H)-carboxylate (intermediate B3) following procedure described for intermediate A2, step 6 (100% yield, white solid). MS (ESI): m/z=196.1 [M+H]$^+$ Intermediate C32: 2-(methylthio)-6-(2,2,2-trifluoroethyl)-7,8-dihydropyrido[4,3-d]pyrimidin-5(6H)-one

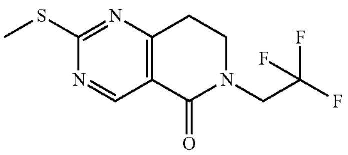 [SMILES: CSc1ncc2c(n1)CCN(CC(F)(F)F)C2=O]

A suspension of ethyl 4-(2-aminoethyl)-2-(methylthio)pyrimidine-5-carboxylate hydrochloride (200 mg, 720 μmol, intermediate B2) in 1,2-dichloroethane (3.5 ml) was cooled to 0° C. A solution of 2,2,2-trifluoroethyl trifluoromethanesulfonate (201 mg, 124 μl, 864 μmol) in 1,2-dichloroethane (0.5 ml) was added, followed by N,N-disiopropylethylamine (285 mg, 377 μl, 2.16 mmol). The reaction mixture was stirred at rt for 20 h and at 70° C. for 3 h. The reaction mixture was diluted with EtOAc and washed twice with water. The organic layer was dried over sodium sulfate and concentrated in vacuo. The residue was diluted with dioxane (2.5 ml). Trimethylaluminium 2 M in toluene (720 μl, 1.44 mmol) was added dropwise. The reaction mixture was heated to 80° C. and stirred for 2 h. The reaction mixture was carefully quenched with water and extracted twice with EtOAc. The organics layers were dried over sodium sulfate and concentrated in vacuo. The crude material was purified by flash chromatography over silica gel using a gradient ethylacetate/heptane 0-100% to provide the title compound as a orange solid (55 mg, 23% yield). MS (ESI): m/z=278.1 [M+H]$^+$

EXAMPLES

Example 1: 2-((5-chloro-2,3-dihydro-1H-inden-2-yl)amino)-6-(oxetan-3-yl)-6,7-dihydro-5H-pyrrolo[3,4-d]pyrimidin-5-one

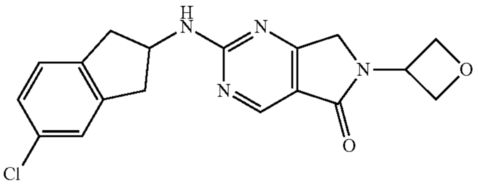 [SMILES: O=C1c2cnc(NC3Cc4ccc(Cl)cc4C3)nc2CN1C1COC1]

A suspension of 2-(methylthio)-6-(oxetan-3-yl)-6,7-dihydro-5H-pyrrolo[3,4-d]pyrimidin-5-one (intermediate C1) (67 mg, 282 μmol) in 1,2-dichloroethane (3 ml) was cooled to 0° C. 3-chloroperoxybenzoic acid (133 mg, 593 μmol) was added. The reaction mixture was allowed to warm to rt and stirred for 1 h. 5-chloro-2,3-dihydro-1H-inden-2-amine hydrochloride (72 mg, 339 μmol, intermediate A1) and N,N-diisopropylethylamine (112 mg, 148 μl, 847 μmol) were added and the stirring was continued at rt for 1 h. The resulting dark red solution was poured into a saturated bicarbonate solution and extracted twice with dichloromethane. The combined organic layers were dried over sodium sulfate and concentrated in vacuo. The crude material was purified by flash chromatography over silica gel using a gradient ethylacetate/heptane 0-100% to provide the title compound as an off-white solid (21 mg, 21% yield). MS (ESI): m/z=357.2 [M+H]$^+$ The following examples 2-36 were prepared in analogy to example 1 from the indicated dihydro-1H-inden-2-amine intermediates A1 or A2 and thio-methyl intermediates C2-32.

| Ex. | Structure | Name | Int. A | Int. C | MS (ESI): m/z, [M + H]$^+$ |
|---|---|---|---|---|---|
| 2 | 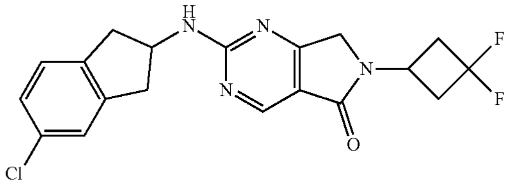 [SMILES: O=C1c2cnc(NC3Cc4ccc(Cl)cc4C3)nc2CN1C1CC(F)(F)C1] | 2-((5-chloro-2,3-dihydro-1H-inden-2-yl)amino)-6-(3-methyloxetan-3-yl)-6,7-dihydro-5H-pyrrolo[3,4-d]pyrimidin-5-one | A1 | C2 | 371.2 |
| 3 | 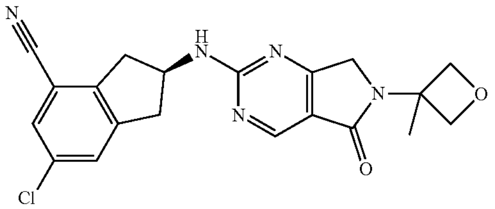 [SMILES: CC1(N2Cc3nc(N[C@H]4Cc5cc(Cl)cc(C#N)c5C4)ncc3C2=O)COC1] | (S)-6-chloro-2-((6-(3-methyloxetan-3-yl)-5-oxo-6,7-dihydro-5H-pyrrolo[3,4-d]pyrimidin-2-yl)amino)-2,3-dihydro-1H-indene-4-carbonitrile | A2 | C2 | 396.3 |
| 4 | 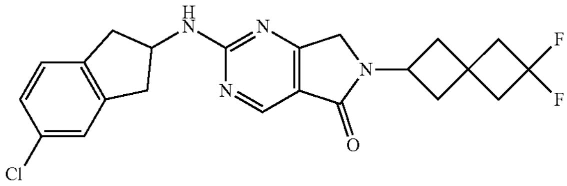 [SMILES: O=C1c2cnc(NC3Cc4ccc(Cl)cc4C3)nc2CN1C1CC2(C1)CC(F)(F)C2] | 2-((5-chloro-2,3-dihydro-1H-inden-2-yl)amino)-6-(6,6-difluorospiro[3.3]heptan-2-yl)-6,7-dihydro-5H-pyrrolo[3,4-d]pyrimidin-5-one | A1 | C3 | 431.1 |
| 5 | 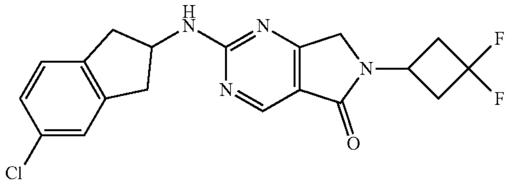 [SMILES: O=C1c2cnc(NC3Cc4ccc(Cl)cc4C3)nc2CN1C1CC(F)(F)C1] | 2-((5-chloro-2,3-dihydro-1H-inden-2-yl)amino)-6-(3,3-difluorocyclobutyl)-6,7-dihydro-5H-pyrrolo[3,4-d]pyrimidin-5-one | A1 | C4 | 391.3 |
| 6 | 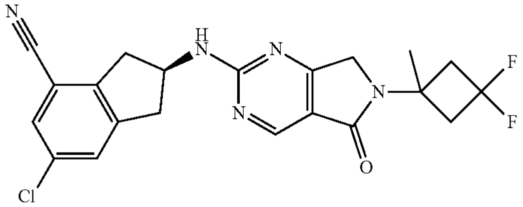 [SMILES: CC1(N2Cc3nc(N[C@H]4Cc5cc(Cl)cc(C#N)c5C4)ncc3C2=O)CC(F)(F)C1] | (S)-6-chloro-2-((6-(3,3-difluoro-1-methylcyclobutyl)-5-oxo-6,7-dihydro-5H-pyrrolo[3,4-d]pyrimidin-2-yl)amino)-2,3-dihydro-1H-indene-4-carbonitrile | A2 | C5 | 430.2 |
| 7 | 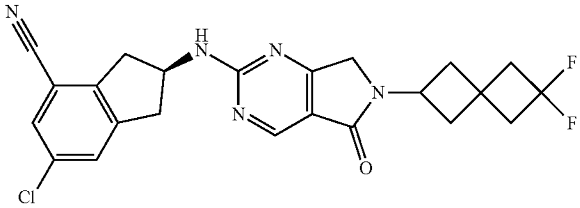 [SMILES: N#Cc1cc(Cl)cc2c1C[C@@H](Nc1ncc3c(n1)CN(C1CC4(C1)CC(F)(F)C4)C3=O)C2] | (S)-6-chloro-2-((6-(6,6-difluorospiro[3.3]heptan-2-yl)-5-oxo-6,7-dihydro-5H-pyrrolo[3,4-d]pyrimidin-2-yl)amino)-2,3-dihydro-1H-indene-4-carbonitrile | A2 | C3 | 456.3 |
| 8 | 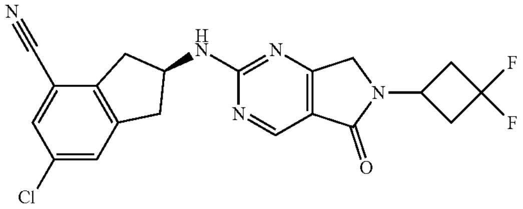 [SMILES: N#Cc1cc(Cl)cc2c1C[C@@H](Nc1ncc3c(n1)CN(C1CC(F)(F)C1)C3=O)C2] | (S)-6-chloro-2-((6-(3,3-difluorocyclobutyl)-5-oxo-6,7-dihydro-5H-pyrrolo[3,4-d]pyrimidin-2-yl)amino)-2,3-dihydro-1H-indene-4-carbonitrile | A2 | C4 | 416.2 |

-continued

| Ex. | Structure | Name | Int. A | Int. C | MS (ESI): m/z, [M + H]+ |
|---|---|---|---|---|---|
| 9 | 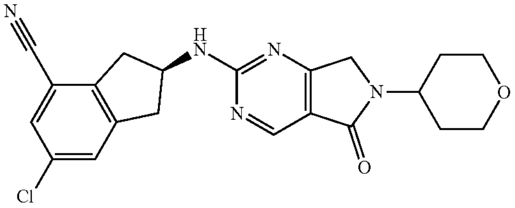 [SMILES: N#Cc1cc(Cl)cc2c1C[C@@H](Nc1ncc3c(n1)CN(C1CCOCC1)C3=O)C2] | (S)-6-chloro-2-((5-oxo-6-(tetrahydro-2H-pyran-4-yl)-6,7-dihydro-5H-pyrrolo[3,4-d]pyrimidin-2-yl)amino)-2,3-dihydro-1H-indene-4-carbonitrile | A2 | C6 | 410.2 |
| 10 | 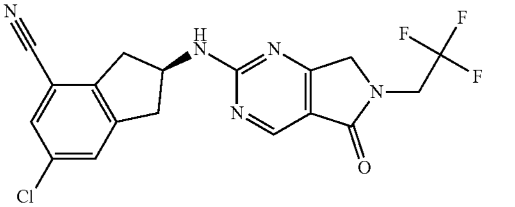 [SMILES: N#Cc1cc(Cl)cc2c1C[C@@H](Nc1ncc3c(n1)CN(CC(F)(F)F)C3=O)C2] | (S)-6-chloro-2-((5-oxo-6-(2,2,2-trifluoroethyl)-6,7-dihydro-5H-pyrrolo[3,4-d]pyrimidin-2-yl)amino)-2,3-dihydro-1H-indene-4-carbonitrile | A2 | C7 | 408.2 |
| 11 | 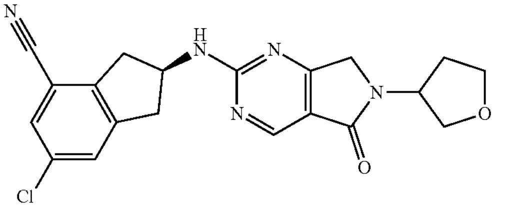 [SMILES: N#Cc1cc(Cl)cc2c1C[C@@H](Nc1ncc3c(n1)CN(C1CCOC1)C3=O)C2] | (S,S) and (S,R)-6-chloro-2-((5-oxo-6-(tetrahydrofuran-3-yl)-6,7-dihydro-5H-pyrrolo[3,4-d]pyrimidin-2-yl)amino)-2,3-dihydro-1H-indene-4-carbonitrile | A2 | C8 | 396.2 |
| 12 | 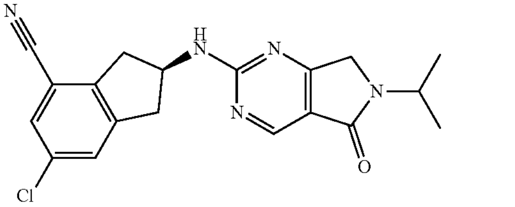 [SMILES: CC(C)N1Cc2nc(N[C@H]3Cc4cc(Cl)cc(C#N)c4C3)ncc2C1=O] | (S)-6-chloro-2-((6-isopropyl-5-oxo-6,7-dihydro-5H-pyrrolo[3,4-d]pyrimidin-2-yl)amino)-2,3-dihydro-1H-indene-4-carbonitrile | A2 | C9 | 368.2 |
| 13 | 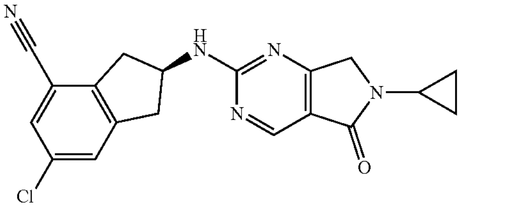 [SMILES: N#Cc1cc(Cl)cc2c1C[C@@H](Nc1ncc3c(n1)CN(C1CC1)C3=O)C2] | (S)-6-chloro-2-((6-cyclopropyl-5-oxo-6,7-dihydro-5H-pyrrolo[3,4-d]pyrimidin-2-yl)amino)-2,3-dihydro-1H-indene-4-carbonitrile | A2 | C10 | 366.2 |
| 14 | 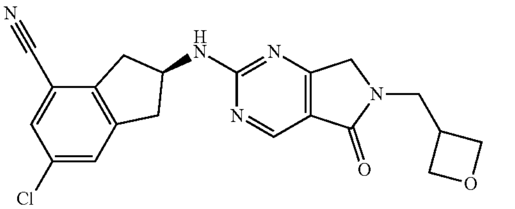 [SMILES: N#Cc1cc(Cl)cc2c1C[C@@H](Nc1ncc3c(n1)CN(CC1COC1)C3=O)C2] | (S)-6-chloro-2-((6-(oxetan-3-ylmethyl)-5-oxo-6,7-dihydro-5H-pyrrolo[3,4-d]pyrimidin-2-yl)amino)-2,3-dihydro-1H-indene-4-carbonitrile | A2 | C11 | 396.2 |
| 15 | 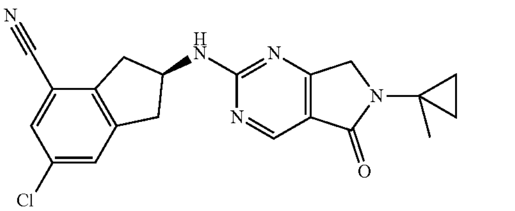 [SMILES: CC1(N2Cc3nc(N[C@H]4Cc5cc(Cl)cc(C#N)c5C4)ncc3C2=O)CC1] | (S)-6-chloro-2-((6-(1-methylcyclopropyl)-5-oxo-6,7-dihydro-5H-pyrrolo[3,4-d]pyrimidin-2-yl)amino)-2,3-dihydro-1H-indene-4-carbonitrile | A2 | C12 | 380.2 |

-continued

| Ex. | Structure | Name | Int. A | Int. C | MS (ESI): m/z, [M + H]+ |
|---|---|---|---|---|---|
| 16 | 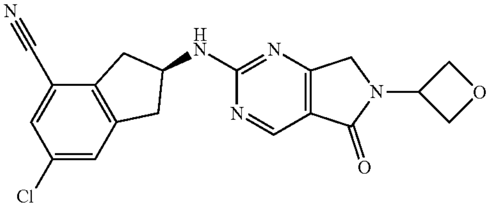 [SMILES: N#Cc1cc(Cl)cc2c1C[C@@H](Nc1ncc3c(n1)CN(C1COC1)C3=O)C2] | (S)-6-chloro-2-((6-(oxetan-3-yl)-5-oxo-6,7-dihydro-5H-pyrrolo[3,4-d]pyrimidin-2-yl)amino)-2,3-dihydro-1H-indene-4-carbonitrile | A2 | C1 | 382.2 |
| 17 | 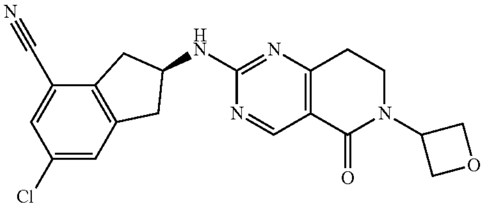 [SMILES: N#Cc1cc(Cl)cc2c1C[C@@H](Nc1ncc3c(n1)CCN(C1COC1)C3=O)C2] | (S)-6-chloro-2-((6-(oxetan-3-yl)-5-oxo-5,6,7,8-tetrahydropyrido[4,3-d]pyrimidin-2-yl)amino)-2,3-dihydro-1H-indene-4-carbonitrile | A2 | C25 | 396.2 |
| 18 | 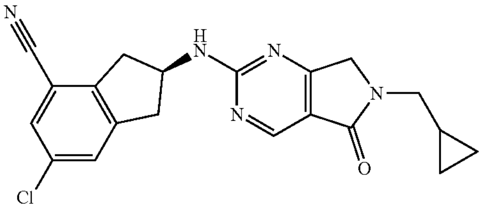 [SMILES: N#Cc1cc(Cl)cc2c1C[C@@H](Nc1ncc3c(n1)CN(CC1CC1)C3=O)C2] | (S)-6-chloro-2-((6-(cyclopropylmethyl)-5-oxo-6,7-dihydro-5H-pyrrolo[3,4-d]pyrimidin-2-yl)amino)-2,3-dihydro-1H-indene-4-carbonitrile | A2 | C13 | 380.2 |
| 19 | 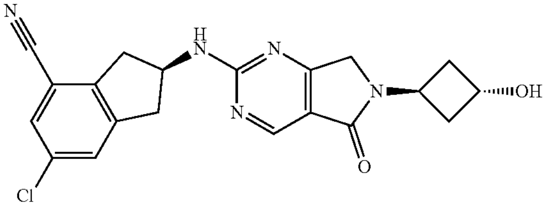 [SMILES: N#Cc1cc(Cl)cc2c1C[C@@H](Nc1ncc3c(n1)CN([C@H]1C[C@H](O)C1)C3=O)C2] | (S)-6-chloro-2-((6-(trans)-3-hydroxycyclobutyl)-5-oxo-6,7-dihydro-5H-pyrrolo[3,4-d]pyrimidin-2-yl)amino)-2,3-dihydro-1H-indene-4-carbonitrile | A2 | C14 | 396.2 |
| 20 | 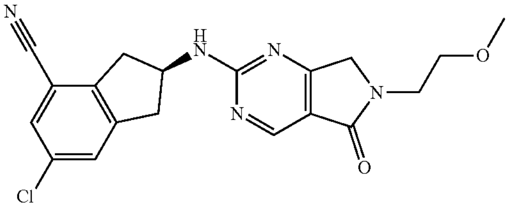 [SMILES: COCCN1Cc2nc(N[C@H]3Cc4cc(Cl)cc(C#N)c4C3)ncc2C1=O] | (S)-6-chloro-2-((6-(2-methoxyethyl)-5-oxo-6,7-dihydro-5H-pyrrolo[3,4-d]pyrimidin-2-yl)amino)-2,3-dihydro-1H-indene-4-carbonitrile | A2 | C15 | 384.2 |
| 21 | 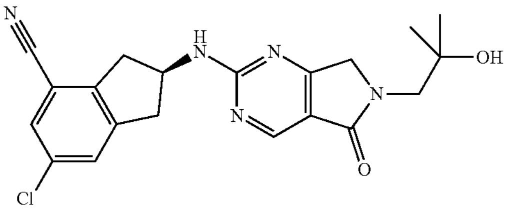 [SMILES: CC(C)(O)CN1Cc2nc(N[C@H]3Cc4cc(Cl)cc(C#N)c4C3)ncc2C1=O] | (S)-6-chloro-2-((6-(2-hydroxy-2-methylpropyl)-5-oxo-6,7-dihydro-5H-pyrrolo[3,4-d]pyrimidin-2-yl)amino)-2,3-dihydro-1H-indene-4-carbonitrile | A2 | C16 | 398.2 |
| 22 | 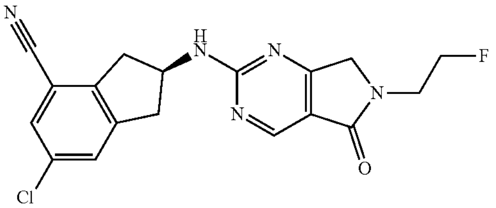 [SMILES: N#Cc1cc(Cl)cc2c1C[C@@H](Nc1ncc3c(n1)CN(CCF)C3=O)C2] | (S)-6-chloro-2-((6-(2-fluoroethyl)-5-oxo-6,7-dihydro-5H-pyrrolo[3,4-d]pyrimidin-2-yl)amino)-2,3-dihydro-1H-indene-4-carbonitrile | A2 | C17 | 372.2 |

-continued

| Ex. | Structure | Name | Int. A | Int. C | MS (ESI): m/z, [M + H]+ |
|---|---|---|---|---|---|
| 23 | 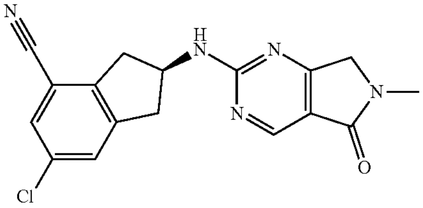 [SMILES: CN1Cc2nc(N[C@H]3Cc4cc(Cl)cc(C#N)c4C3)ncc2C1=O] | (S)-6-chloro-2-((6-methyl-5-oxo-6,7-dihydro-5H-pyrrolo[3,4-d]pyrimidin-2-yl)amino)-2,3-dihydro-1H-indene-4-carbonitrile | A2 | C18 | 340.2 |
| 24 | 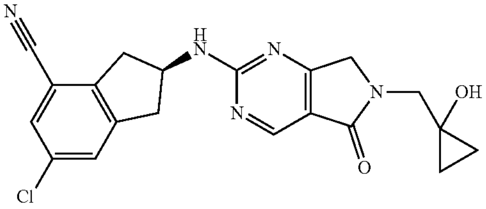 [SMILES: N#Cc1cc(Cl)cc2c1C[C@@H](Nc1ncc3c(n1)CN(CC1(O)CC1)C3=O)C2] | (S)-6-chloro-2-((6-((l-hydroxycyclopropyl)methyl)-5-oxo-6,7-dihydro-5H-pyrrolo[3,4-d]pyrimidin-2-yl)amino)-2,3-dihydro-1H-indene-4-carbonitrile | A2 | C19 | 396.2 |
| 25 | 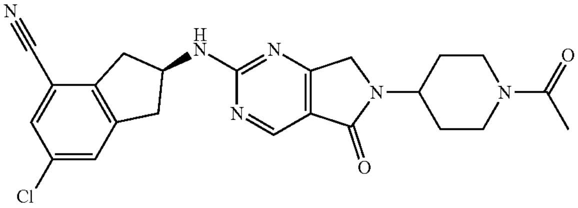 [SMILES: CC(=O)N1CCC(N2Cc3nc(N[C@H]4Cc5cc(Cl)cc(C#N)c5C4)ncc3C2=O)CC1] | (S)-2-((6-(l-acetylpiperidin-4-yl)-5-oxo-6,7-dihydro-5H-pyrrolo[3,4-d]pyrimidin-2-yl)amino)-6-chloro-2,3-dihydro-1H-indene-4-carbonitrile | A2 | C20 | 451.3 |
| 26 | 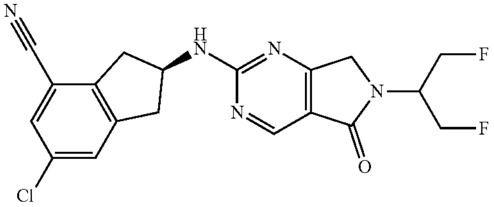 [SMILES: N#Cc1cc(Cl)cc2c1C[C@@H](Nc1ncc3c(n1)CN(C(CF)CF)C3=O)C2] | (S)-6-chloro-2-((6-(l,3-difluoropropan-2-yl)-5-oxo-6,7-dihydro-5H-pyrrolo[3,4-d]pyrimidin-2-yl)amino)-2,3-dihydro-1H-indene-4-carbonitrile | A2 | C21 | 404.2 |
| 27 | 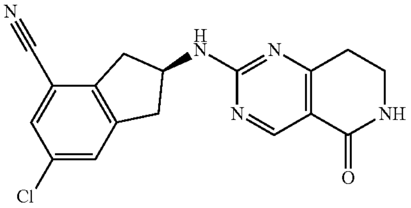 [SMILES: N#Cc1cc(Cl)cc2c1C[C@@H](Nc1ncc3c(n1)CCNC3=O)C2] | (S)-6-chloro-2-((5-oxo-5,6,7,8-tetrahydropyrido [4,3-d]pyrimidin-2-yl)amino)-2,3-dihydro-1H-indene-4-carbonitrile | A2 | C31 | 340.2 |
| 28 | 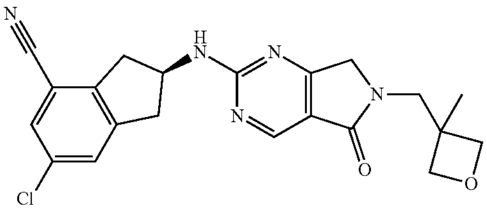 [SMILES: CC1(CN2Cc3nc(N[C@H]4Cc5cc(Cl)cc(C#N)c5C4)ncc3C2=O)COC1] | (S)-6-chloro-2-((6-((3-methyloxetan-3-yl)methyl)-5-oxo-6,7-dihydro-5H-pyrrolo[3,4-d]pyrimidin-2-yl)amino)-2,3-dihydro-1H-indene-4-carbonitrile | A2 | C22 | 410.3 |
| 29 | 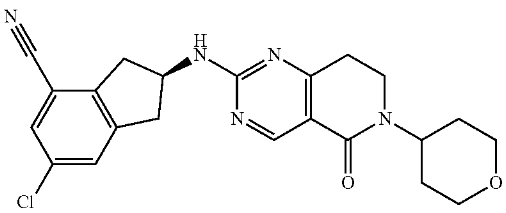 [SMILES: N#Cc1cc(Cl)cc2c1C[C@@H](Nc1ncc3c(n1)CCN(C1CCOCC1)C3=O)C2] | (S)-6-chloro-2-((5-oxo-6-(tetrahydro-2H-pyran-4-yl)-5,6,7,8-tetrahydropyrido[4,3-d]pyrimidin-2-yl)amino)-2,3-dihydro-1H-indene-4-carbonitrile | A2 | C26 | 424.3 |

-continued

| Ex. | Structure | Name | Int. A | Int. C | MS (ESI): m/z, [M + H]+ |
|---|---|---|---|---|---|
| 30 | 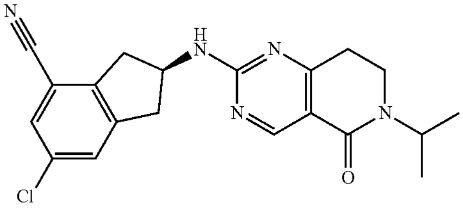 [SMILES: CC(C)N1CCc2nc(N[C@H]3Cc4cc(Cl)cc(C#N)c4C3)ncc2C1=O] | (S)-6-chloro-2-((6-isopropyl-5-oxo-5,6,7,8-tetrahydropyrido[4,3-d]pyrimidin-2-yl)amino)-2,3-dihydro-1H-indene-4-carbonitrile | A2 | C27 | 382.2 |
| 31 | 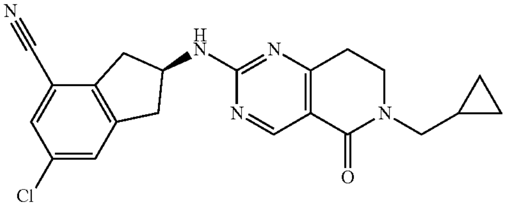 [SMILES: N#Cc1cc(Cl)cc2c1C[C@@H](Nc1ncc3c(n1)CCN(CC1CC1)C3=O)C2] | (S)-6-chloro-2-((6-(cyclopropylmethyl)-5-oxo-5,6,7,8-tetrahydropyrido[4,3-d]pyrimidin-2-yl)amino)-2,3-dihydro-1H-indene-4-carbonitrile | A2 | C28 | 394.2 |
| 32 | 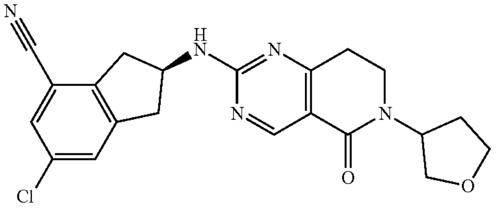 [SMILES: N#Cc1cc(Cl)cc2c1C[C@@H](Nc1ncc3c(n1)CCN(C1CCOC1)C3=O)C2] | (S,S) and (S,R)-6-chloro-2-((5-oxo-6-(tetrahydrofuran-3-yl)-5,6,7,8-tetrahydropyrido[4,3-d]pyrimidin-2-yl)amino)-2,3-dihydro-1H-indene-4-carbonitrile | A2 | C29 | 410.2 |
| 33 | 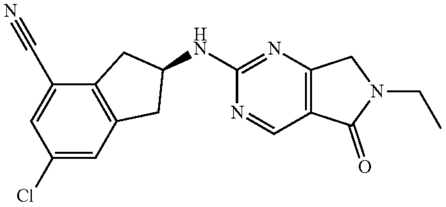 [SMILES: CCN1Cc2nc(N[C@H]3Cc4cc(Cl)cc(C#N)c4C3)ncc2C1=O] | (S)-6-chloro-2-((6-ethyl-5-oxo-6,7-dihydro-5H-pyrrolo[3,4-d]pyrimidin-2-yl)amino)-2,3-dihydro-1H-indene-4-carbonitrile | A2 | C23 | 354.2 |
| 34 | 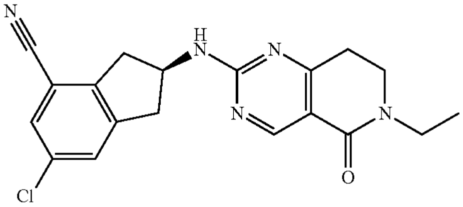 [SMILES: CCN1CCc2nc(N[C@H]3Cc4cc(Cl)cc(C#N)c4C3)ncc2C1=O] | (S)-6-chloro-2-((6-ethyl-5-oxo-5,6,7,8-tetrahydropyrido[4,3-d]pyrimidin-2-yl)amino)-2,3-dihydro-1H-indene-4-carbonitrile | A2 | C30 | 368.2 |
| 35 | 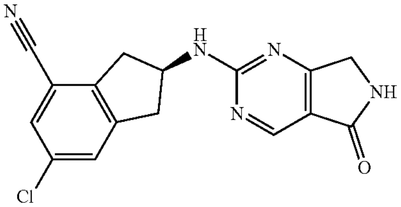 [SMILES: N#Cc1cc(Cl)cc2c1C[C@@H](Nc1ncc3c(n1)CNC3=O)C2] | (S)-6-chloro-2-((5-oxo-6,7-dihydro-5H-pyrrolo[3,4-d]pyrimidin-2-yl)amino)-2,3-dihydro-1H-indene-4-carbonitrile | A2 | C24 | 326.1 |
| 36 | 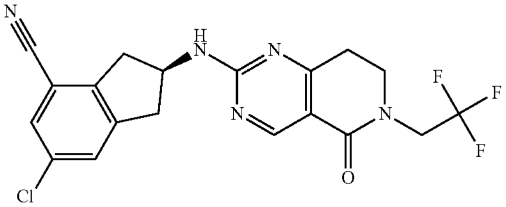 [SMILES: N#Cc1cc(Cl)cc2c1C[C@@H](Nc1ncc3c(n1)CCN(CC(F)(F)F)C3=O)C2] | (S)-6-chloro-2-((5-oxo-6-(2,2,2-trifluoroethyl)-5,6,7,8-tetrahydropyrido[4,3-d]pyrimidin-2-yl)amino)-2,3-dihydro-1H-indene-4-carbonitrile | A2 | C32 | 422.2 |

Example A

A compound of formula (I) can be used in a manner known per se as the active ingredient for the production of tablets of the following composition:

Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I)

(I)

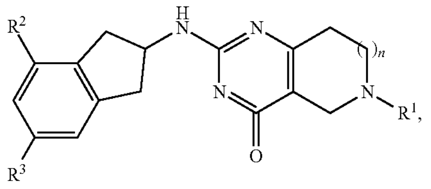

or a pharmaceutically acceptable salt thereof, wherein:

$R^1$ is selected from the group consisting of i) H,
ii) $C_{1-6}$-alkyl,
iii) $C_{3-8}$-cycloalkyl,
iv) $C_{3-8}$-cycloalkylalkyl,
v) $C_{1-6}$-alkoxy,
vi) $C_{1-6}$-alkoxy-$C_{1-6}$-alkyl,
vii) heterocycloalkyl,
viii) heterocycloalkylalkyl,
ix) substituted $C_{3-8}$-cycloalkyl,
x) substituted $C_{3-8}$-cycloalkylalkyl,
xi) substituted heterocycloalkyl,
xii) substituted heterocycloalkylalkyl,
xiii) halo-$C_{1-6}$-alkyl, and
xiv) hydroxy-$C_{1-6}$-alkyl, wherein substituted $C_{3-8}$-cycloalkyl or substituted heterocycloalkyl are substituted with one or more substituents selected from the group consisting of H, $C_{1-6}$-alkyl, halogen, hydroxy, and $C_{1-6}$-carbonyl;

$R^2$ is selected from the group consisting of i) H,
ii) halogen,
iii) halo-$C_{1-6}$-alkyl,
iv) $C_{1-6}$-alkyl, and
v) cyano, wherein at least one of $R^1$ and $R^2$ is other than H;

$R^3$ is selected from the group consisting of i) H, and
ii) halogen; and n is 0 or 1.

2. A compound according to claim 1, or a pharmaceutically acceptable salt thereof, wherein $R^3$ is halogen.

3. A compound according to claim 1, or a pharmaceutically acceptable salt thereof, wherein $R^3$ is Cl.

4. A compound according to claim 1, or a pharmaceutically acceptable salt thereof, wherein $R^2$ is selected from the group consisting of i) H, and
ii) cyano.

5. A compound according to claim 1, or a pharmaceutically acceptable salt thereof, wherein $R^1$ is selected from the group consisting of i) H,
ii) $C_{1-6}$-alkyl,
iii) $C_{3-8}$-cycloalkyl,
iv) $C_{3-8}$-cycloalkylalkyl,
v) $C_{1-6}$-alkoxy,
vi) $C_{1-6}$-alkoxy-$C_{1-6}$-alkyl,
vii) heterocycloalkyl,
viii) heterocycloalkylalkyl,
ix) substituted $C_{3-8}$-cycloalkyl,
x) substituted $C_{3-8}$-cycloalkylalkyl,
xi) substituted heterocycloalkyl,
xii) substituted heterocycloalkylalkyl,
xiii) halo-$C_{1-6}$-alkyl, and
xiv) hydroxy-$C_{1-6}$-alkyl, wherein substituted $C_{3-8}$-cycloalkyl or substituted heterocycloalkyl are substituted with one or more substituents selected from the group consisting of H, $C_{1-6}$-alkyl, halogen, hydroxy, and $C_{1-6}$-carbonyl; and wherein heterocycloalkyl is a 4-6 atom ring system comprising one heteroatom selected from N and O.

6. A compound according to claim 1, or a pharmaceutically acceptable salt thereof, wherein $R^3$ is Cl, $R^2$ is H or cyano, and $R^1$ is selected from the group consisting of i) H,
ii) $C_{1-6}$-alkyl,
iii) $C_{3-8}$-cycloalkyl,
iv) $C_{3-8}$-cycloalkylalkyl,
v) $C_{1-6}$-alkoxy,
vi) $C_{1-6}$-alkoxy-$C_{1-6}$-alkyl,
vii) heterocycloalkyl,
viii) heterocycloalkylalkyl,
ix) substituted $C_{3-8}$-cycloalkyl,
x) substituted $C_{3-8}$-cycloalkylalkyl,
xi) substituted heterocycloalkyl,
xii) substituted heterocycloalkylalkyl,
xiii) halo-$C_{1-6}$-alkyl, and
xiv) hydroxy-$C_{1-6}$-alkyl, wherein substituted $C_{3-8}$-cycloalkyl or substituted heterocycloalkyl are substituted with one or more substituents selected from the group consisting of H, $C_{1-6}$-alkyl, halogen, hydroxy, and $C_{1-6}$-carbonyl;

wherein heterocycloalkyl is a 4-6 atom ring system comprising one heteroatom selected from N and O;

wherein at least one of $R^1$ and $R^2$ is other than H; and n is 0 or 1.

7. A compound according to claim 1, selected from the group consisting of 2-((5-chloro-2,3-dihydro-1H-inden-2-yl)amino)-6-(oxetan-3-yl)-6,7-dihydro-5H-pyrrolo[3,4-d]pyrimidin-5-one;

2-((5-chloro-2,3-dihydro-1H-inden-2-yl)amino)-6-(3-methyloxetan-3-yl)-6,7-dihydro-5H-pyrrolo[3,4-d]pyrimidin-5-one;

(S)-6-chloro-2-((6-(3-methyloxetan-3-yl)-5-oxo-6,7-dihydro-5H-pyrrolo[3,4-d]pyrimidin-2-yl)amino)-2,3-dihydro-1H-indene-4-carbonitrile;

2-((5-chloro-2,3-dihydro-1H-inden-2-yl)amino)-6-(6,6-difluorospiro[3.3]heptan-2-yl)-6,7-dihydro-5H-pyrrolo[3,4-d]pyrimidin-5-one;

2-((5-chloro-2,3-dihydro-1H-inden-2-yl)amino)-6-(3,3-difluorocyclobutyl)-6,7-dihydro-5H-pyrrolo[3,4-d]pyrimidin-5-one;

(S)-6-chloro-2-((6-(3,3-difluoro-1-methylcyclobutyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(6,6-difluorospiro[3.3]heptan-2-yl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(3,3-difluorocyclobutyl)-5-oxo-6,7-dihydro-5H-pyrrolo[3,4-d]pyrimidin-2-yl)amino)-2,3-dihydro-1H-indene-4-carbonitrile;

(S)-6-chloro-2-((5-oxo-6-(tetrahydro-2H-pyran-4-yl)-6,7-dihydro-5H-pyrrolo[3,4-d]pyrimidin-2-yl)amino)-2,3-dihydro-1H-indene-4-carbonitrile;

(S)-6-chloro-2-((5-oxo-6-(2,2,2-trifluoroethyl)-6,7-dihydro-5H-pyrrolo[3,4-d]pyrimidin-2-yl)amino)-2,3-dihydro-1H-indene-4-carbonitrile;

(S,S) and (S,R)-6-chloro-2-((5-oxo-6-(tetrahydrofuran-3-yl)-6,7-dihydro-5H-pyrrolo[3,4-d]pyrimidin-2-yl)amino)-2,3-dihydro-1H-indene-4-carbonitrile;

(S)-6-chloro-2-((6-isopropyl-5-oxo-6,7-dihydro-5H-pyrrolo[3,4-d]pyrimidin-2-yl)amino)-2,3-dihydro-1H-indene-4-carbonitrile;

(S)-6-chloro-2-((6-cyclopropyl-5-oxo-6,7-dihydro-5H-pyrrolo[3,4-d]pyrimidin-2-yl)amino)-2,3-dihydro-1H-indene-4-carbonitrile;

(S)-6-chloro-2-((6-(oxetan-3-ylmethyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(1-methylcyclopropyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(oxetan-3-yl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(oxetan-3-yl)-5-oxo-5,6,7,8-tetrahydropyrido[4,3-d]pyrimidin-2-yl)amino)-2,3-dihydro-1H-indene-4-carbonitrile;

(S)-6-chloro-2-((6-(cyclopropylmethyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-((1r,3S)-3-hydroxycyclobutyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(2-methoxyethyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(2-hydroxy-2-methylpropyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-(2-fluoroethyl)-5-oxo-6,7-dihydro-5H-pyrrolo[3,4-d]pyrimidin-2-yl)amino)-2,3-dihydro-1H-indene-4-carbonitrile;

(S)-6-chloro-2-((6-methyl-5-oxo-6,7-dihydro-5H-pyrrolo[3,4-d]pyrimidin-2-yl)amino)-2,3-dihydro-1H-indene-4-carbonitrile;

(S)-6-chloro-2-((6-((1-hydroxycyclopropyl)methyl)-5-oxo-6,7-dihydro-5H-pyrrolo[3,4-d]pyrimidin-2-yl)amino)-2,3-dihydro-1H-indene-4-carbonitrile;

(S)-2-((6-(1-acetylpiperidin-4-yl)-5-oxo-6,7-dihydro-5H-pyrrolo[3,4-d]pyrimidin-2-yl)amino)-6-chloro-2,3-dihydro-1H-indene-4-carbonitrile;

(S)-6-chloro-2-((6-(1,3-difluoropropan-2-yl)-5-oxo-6,7-dihydro-5H-pyrrolo[3,4-d]pyrimidin-2-yl)amino)-2,3-dihydro-1H-indene-4-carbonitrile;

(S)-6-chloro-2-((5-oxo-5,6,7,8-tetrahydropyrido[4,3-d]pyrimidin-2-yl)amino)-2,3-dihydro-1H-indene-4-carbonitrile;

(S)-6-chloro-2-((6-((3-methyloxetan-3-yl)methyl)-5-oxo-6,7-dihydro-5H-pyrrolo[3,4-d]pyrimidin-2-yl)amino)-2,3-dihydro-1H-indene-4-carbonitrile;

(S)-6-chloro-2-((5-oxo-6-(tetrahydro-2H-pyran-4-yl)-5,6,7,8-tetrahydropyrido[4,3-d]pyrimidin-2-yl)amino)-2,3-dihydro-1H-indene-4-carbonitrile;

(S)-6-chloro-2-((6-isopropyl-5-oxo-5,6,7,8-tetrahydropyrido[4,3-d]pyrimidin-2-yl)amino)-2,3-dihydro-1H-indene-4-carbonitrile;

(S)-6-chloro-2-((6-(cyclopropylmethyl)-5-oxo-5,6,7,8-tetrahydropyrido[4,3-d]pyrimidin-2-yl)amino)-2,3-dihydro-1H-indene-4-carbonitrile;

(S,S) and (S,R) 6-chloro-2-((5-oxo-6-(tetrahydrofuran-3-yl)-5,6,7,8-tetrahydropyrido[4,3-d]pyrimidin-2-yl)amino)-2,3-dihydro-1H-indene-4-carbonitrile;

(S)-6-chloro-2-((6-ethyl-5-oxo-6,7-dihydro-5H-pyrrolo[3,4-d]pyrimidin-2-yl)amino)-2,3-dihydro-1H-indene-4-carbonitrile;

(S)-6-chloro-2-((6-ethyl-5-oxo-5,6,7,8-tetrahydropyrido[4,3-d]pyrimidin-2-yl)amino)-2,3-dihydro-1H-indene-4-carbonitrile;

(S)-6-chloro-2-((5-oxo-6,7-dihydro-5H-pyrrolo[3,4-d]pyrimidin-2-yl)amino)-2,3-dihydro-1H-indene-4-carbonitrile; and (S)-6-chloro-2-((5-oxo-6-(2,2,2-trifluoroethyl)-5,6,7,8-tetrahydropyrido[4,3-d]pyrimidin-2-yl)amino)-2,3-dihydro-1H-indene-4-carbonitrile;

or a pharmaceutically acceptable salt thereof.

8. A process to prepare a compound according to claim 1, or a pharmaceutically acceptable salt thereof, the process comprising the reaction of a compound of formula (II) in the presence of a compound of formula (III) to provide a compound of formula (I), wherein $R^1$, $R^2$, $R^3$, and n are as defined in claim 1:

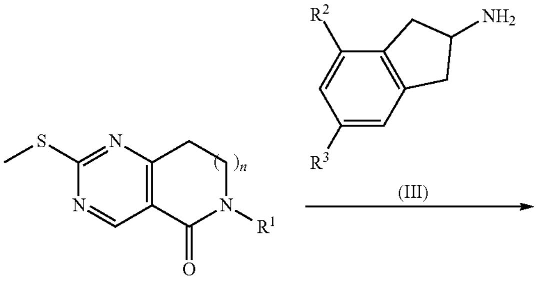

(II)

-continued
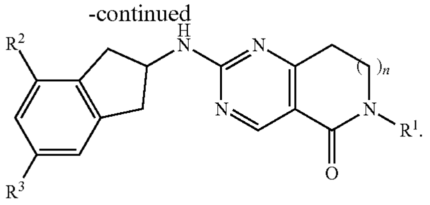
(I)
9. A pharmaceutical composition comprising a compound according to claim 1, or a pharmaceutically acceptable salt thereof, and a therapeutically inert carrier.
* * * * *